(12) United States Patent
Wu et al.

(10) Patent No.: US 10,124,054 B2
(45) Date of Patent: Nov. 13, 2018

(54) VACCINE COMBINATION AGAINST MULTIPLE DENGUE VIRUS SEROTYPES AND PREPARATION AND APPLICATION THEREOF

(71) Applicant: National Tsing Hua University, Hsinchu (TW)

(72) Inventors: Suh-Chin Wu, Hsinchu (TW); Hsiao-Han Lin, Hsinchu (TW); Meng-Ju Tsai, Hsinchu (TW); Guan-Cheng Lin, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/494,945

(22) Filed: Apr. 24, 2017

(65) Prior Publication Data

US 2018/0133302 A1 May 17, 2018

(30) Foreign Application Priority Data

Nov. 15, 2016 (TW) .............................. 105137299 A

(51) Int. Cl.
*A61K 39/12* (2006.01)
*C12N 7/00* (2006.01)
*A61K 39/00* (2006.01)

(52) U.S. Cl.
CPC ................ *A61K 39/12* (2013.01); *C12N 7/00* (2013.01); *A61K 2039/5254* (2013.01); *A61K 2039/545* (2013.01); *A61K 2039/575* (2013.01); *A61K 2039/70* (2013.01); *C12N 2770/24121* (2013.01); *C12N 2770/24122* (2013.01); *C12N 2770/24134* (2013.01); *C12N 2770/24171* (2013.01)

(58) Field of Classification Search
None
See application file for complete search history.

(56) References Cited

U.S. PATENT DOCUMENTS

| 9,713,638 B2 * | 7/2017 | Stinchcomb | ........... A61K 39/12 |
| 2014/0205624 A1 * | 7/2014 | Song | ..................... A61K 39/12 424/192.1 |

OTHER PUBLICATIONS

Valdes et al. The Chimeric Protein Domain III-Capsid of Dengue Virus Serotype 2 (DEN-2) Successfully Boosts Neutralizing Antibodies Generated in Monkeys upon Infection with DEN-2. Clinical and Vaccine Immunology, Mar. 2011, vol. 18, No. 3, p. 455-459.*
Liu et al. Immunogenicity and Efficacy of Flagellin-Envelope Fusion Dengue Vaccines in Mice and Monkeys. Clin Vaccine Immunol. 2015. 22:516-525.*

* cited by examiner

*Primary Examiner* — Nianxiang Zou
(74) *Attorney, Agent, or Firm* — WPAT, PC

(57) ABSTRACT

Provided is a vaccine combination against multiple dengue virus serotypes and preparation thereof. The vaccine combination includes a first vaccine and a second vaccine, wherein the first vaccine includes a live-attenuated dengue virus and a live-attenuated chimeric dengue virus, and the second vaccine includes a plurality type of recombinant flagellin and envelope domain III fusion proteins, wherein an envelope domain III of each type of the recombinant flagellin and envelope domain III fusion proteins is derived from a different dengue virus serotype. Also provided is a method of preventing or treating viral infection by multiple dengue virus serotypes in a subject using the vaccine combination, including the steps of administering the first and then the second vaccines at a time interval of about 1-5 weeks.

6 Claims, 18 Drawing Sheets

VACCINE COMBINATION AGAINST MULTIPLE DENGUE VIRUS SEROTYPES AND PREPARATION AND APPLICATION THEREOF

CROSS-REFERENCE TO RELATED APPLICATION

This application claims priority of Taiwan patent application No. 105137299, filed on Nov. 15, 2016, the content of which is incorporated herein in its entirety by reference.

BACKGROUND OF THE INVENTION

1. Field of the Invention

The present invention relates to a vaccine combination and preparation and application thereof. Particularly, the present invention relates to a vaccine combination and the use and manufacture thereof.

2. The Prior Art

Dengue, an anthropod-borne viral disease transmitted to human via mosquitoes, mainly occurs in tropical and subtropical regions. According to the statistics of World Health Organization (WHO) in 2014, around 390 million dengue virus infections were estimated to occur each year in over 100 countries, and almost half of the world population is under threat of dengue virus. Patients infected by dengue virus exhibit symptoms ranging from milder dengue fever to life-threatening dengue hemorrhagic fever. Therefore, prevention and treatment of dengue infection has emerged as a public health issue of increasing concern.

Dengue virus (DENV) belongs to the family Flaviviridae and the genus *Flavivirus* and exists as four antigenic ally distinct serotypes, namely dengue virus type 1 (DENV1), type 2 (DENV2), type 3 (DENV3), and type 4 (DENV4). Dengue virus is an enveloped virus with an icosahedral capsid and a single stranded positive sense RNA genome. This genome consists of about 10,700 nucleotides and encodes a polyprotein, which may be processed through post-transcriptional modification into three structural proteins and seven nonstructural proteins. The three structural proteins are the capsid (abbreviated as C) protein, the precursor membrane (abbreviated as prM) protein, and the envelope (abbreviated as E) protein. Among them, the envelope protein, as a glycoprotein distributed on the surface of the viral envelope, participates in host cell receptor binding to the virus, mediates fusion of viral envelope and cell membrane, and affects viral entry into cells. Thus, it is a major target for humoral immunity. Structurally, the envelope protein consists of three ectodomains, namely domain I (DI), domain II (DII), and domain III (DIII), and a stem-anchor region, wherein domain III is the receptor binding domain. There are studies showing that most potent neutralizing antibodies recognize epitopes in domain III.

A variety of dengue vaccine candidates are under current research, including live-attenuated virus (LAV), purified inactivated virus (PIV), recombinant subunits, DNA plasmid vectors, and viral vectors. However, there are still no effective vaccines against dengue diseases. One of the reasons is that when patients are infected twice with different serotypes of dengue viruses, these patients with secondary infection tend to get infected more easily and develop more severe symptoms because of antibody-dependent enhancement, which is caused by an interaction between cross-reactive antibodies elicited by the primary infection and the heterologous virus upon the secondary infection, leading to facilitated viral infection. Therefore, it is of great necessity to develop a vaccine against multiple dengue virus serotypes, particularly a vaccine capable of inhibiting infection by all four serotypes of dengue viruses.

SUMMARY OF THE INVENTION

As a result, the present invention provides a vaccine combination against multiple dengue virus serotypes, including a first vaccine and a second vaccine, wherein the first vaccine includes a live-attenuated dengue virus and a live-attenuated chimeric dengue virus, and the second vaccine includes a plurality type of recombinant flagellin and envelope domain III fusion proteins, wherein an envelope domain III of each type of the recombinant flagellin and envelope domain III fusion proteins is derived from a different dengue virus serotype, and wherein the vaccine combination provides protection against more dengue viruses serotypes than the live-attenuated dengue viruses in the first vaccine.

In another aspect, the present invention provides a method of preventing or treating viral infection by multiple dengue virus serotypes in a subject using the abovementioned vaccine combination, including the steps of: (a) administering to the subject a first vaccine including a live-attenuated dengue virus and a live-attenuated chimeric dengue virus; and (b) administering to the subject a second vaccine including a plurality type of recombinant flagellin and envelope domain III fusion proteins, wherein an envelope domain III of each type of the recombinant flagellin and envelope domain III fusion proteins is derived from a different dengue virus serotype, wherein the vaccine combination provides protection against more dengue virus serotypes than the live-attenuated dengue viruses in the first vaccine.

In one embodiment of the present invention, the live-attenuated dengue virus is a live-attenuated dengue virus type 4 in an amount of at least $10^4$ FFU; the live-attenuated chimeric dengue virus is a live-attenuated type 2/type 4 chimeric dengue virus in an amount of at least $10^4$ FFU, and the live-attenuated type 2/type 4 chimeric dengue virus expresses a precursor membrane protein and an envelope protein both derived from dengue virus type 2; and the recombinant flagellin and envelope domain III fusion proteins are at least two selected from the group consisting of a recombinant flagellin-dengue virus type 1 envelope domain III fusion protein, a recombinant flagellin-dengue virus type 2 envelope domain III fusion protein, a recombinant flagellin-dengue virus type 3 envelope domain III fusion protein, a recombinant flagellin-dengue virus type 4 envelope domain III fusion protein, and combinations thereof, and each of the recombinant flagellin and envelope domain III fusion proteins is in an amount of at least 20 µg.

In another embodiment of the present invention, the second vaccine is administered 1-5 weeks, preferably 3 weeks, after the first vaccine.

In one further aspect, the present invention provides a method of preparing the vaccine combination previously described, including the steps of: (a) preparing a live-attenuated dengue virus and a live-attenuated chimeric dengue virus and then mixing the live-attenuated dengue virus and the live-attenuated chimeric dengue virus at a number ratio of 2:1 to 1:2, preferably 1:1, to obtain a first vaccine; and (b) preparing a plurality type of recombinant flagellin and envelope domain III fusion proteins and then mixing the plurality type of flagellin and envelope domain III fusion proteins to obtain a second vaccine.

In another further aspect, the present invention provides a method of preventing or treating viral infection by multiple dengue virus serotypes in a subject, including the steps of: (a) administering to the subject a first vaccine including a plurality type of adenoviral vectors expressing a precursor membrane protein and an envelope protein, wherein the precursor membrane protein and the envelope protein expressed by each type of the adenoviral vectors are derived from a different dengue virus serotype; and (b) administering to the subject a second vaccine including a plurality type of recombinant flagellin and envelope domain III fusion proteins or a combination of a live-attenuated dengue virus and a live-attenuated chimeric dengue virus, wherein an envelope domain III of each type of the recombinant flagellin and envelope domain III fusion proteins is derived from a different dengue virus serotype.

The vaccine combination of the present invention can effectively elicit neutralizing antibodies against the four dengue virus serotypes in a subject based on heterologous prime-boost immunization of the subject with the first vaccine containing a live-attenuated dengue virus and a live-attenuated chimeric dengue virus and a second vaccine containing a plurality type of recombinant flagellin and envelope domain III fusion proteins. Therefore, it may enhance immunity against dengue virus infection in a subject and alleviate symptoms resulting from such infection.

The present invention is further explained in the following drawings and examples. It is understood that the examples given below do not, however, limit the scope of the invention, and it will be evident to those skilled in the art that modifications can be made without departing from the scope of the appended claims.

BRIEF DESCRIPTION OF THE DRAWINGS

Figures 12A, 12B, 12C, 12D:
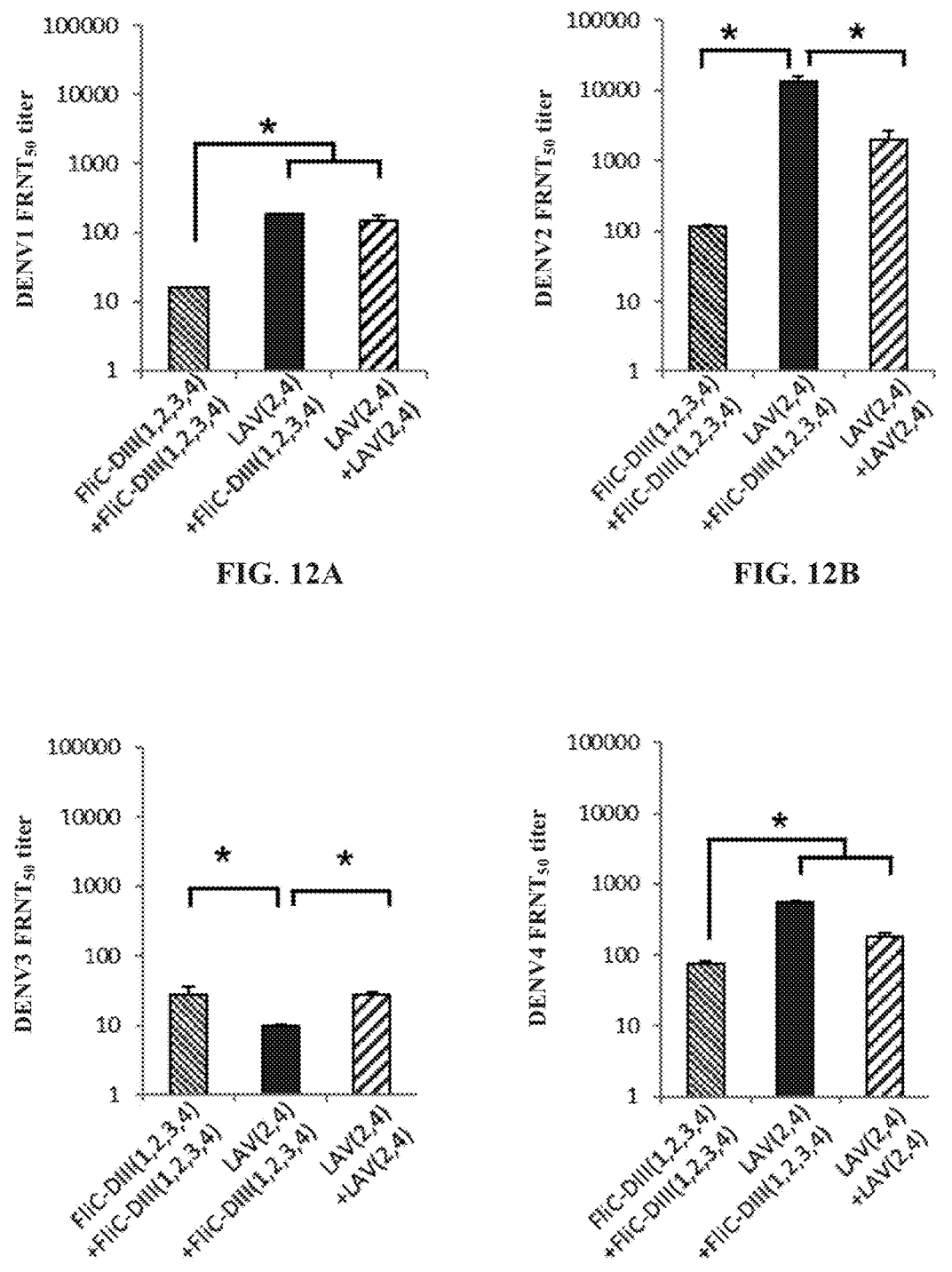

FIGS. 12A-12D show serum neutralizing antibody titers, calculated based on FIGS. 11A-11D, against dengue virus type 1, type 2, type 3, or type 4 for the AG129 mice receiving different immunizations;

DETAILED DESCRIPTION OF THE PREFERRED EMBODIMENT

Definition

Figure 1A:
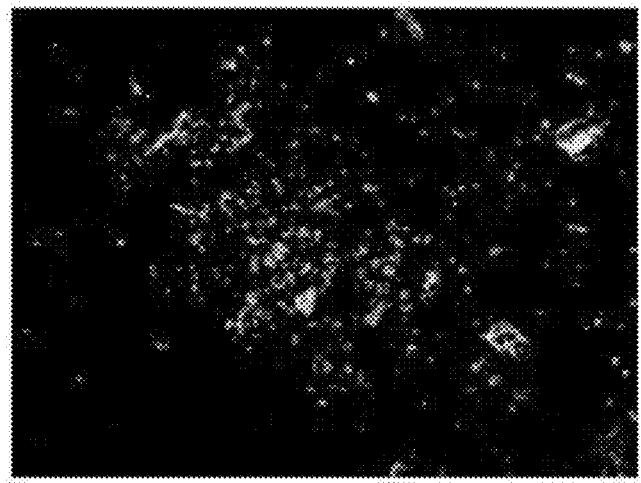
FIGS. 1A-1B show micrographs of Vero E6 cells at 6 days post-infection by live-attenuated dengue virus DENV4 Δ30 and the live-attenuated chimeric dengue virus DENV2/4 Δ30, respectively.

Numerical quantities given herein are approximate, and experimental values may vary within 20 percent, preferably within 10 percent, and most preferably within 5 percent. Thus, the terms "about" and "approximately" refer to within 20 percent, preferably within 10 percent, and most preferably within 5 percent of a given value or range.

As used herein, the term "formulations" is interchangeable with the term "combinations".

Materials and Methods

Cell Culture

Cells used in the following examples included Vero cells (ATCC CCL-81) and Vero E6 cells (ATCC CRL-1586) from African green monkey, mosquito cell line C6/36 (ATCC CRL-1660), and human embryonic kidney 293A cells (ATCC CRL-1573). Vero cells and Vero E6 cells were cultured in Minimum Essential Medium (MEM; Invitrogen) supplemented with 10% fetal bovine serum (FBS) and 100 U/ml penicillin and streptomycin at 37° C. in 5% $CO_2$. C6/36 cells were cultured in Leibovitz's L-15 medium (Invitrogen) supplemented with 10% FBS, 0.3% tryptose phosphate broth (TPB), 1% non-essential amino acids (NEAA), 25 mM HEPES and 100 U/ml penicillin and streptomycin at 28° C. in 5% $CO_2$. 293A cells were cultured in Dulbecco's Modified Essential Medium (DMEM; Invitrogen) supplemented with 5% fetal bovine serum (FBS) and 100 U/ml penicillin and streptomycin at 37° C. in 5% $CO_2$.

Preparation of Wild-Type Dengue Viruses

In the following examples, dengue virus type 1 strain Hawaii (DENV1-Hawaii; EU848545), dengue virus type 2 strain NGC (DENV2-NGC; M29095), and dengue virus type 3 strain H87 (DENV3-H87; M93130) were used. These viruses were prepared from the supernatant of C6/36 cell culture infected with each of the abovementioned viruses and were stored at −80° C.

Mice Immunization

BALB/c mice at the age of 6-8 weeks or AG129 mice at the age of 9 weeks were used for immunization in the examples of the present invention, since live-attenuated dengue virus was able to replicate in AG129 mice. In the following examples, vaccines containing a live-attenuated dengue virus or an adenoviral vector were administered via intraperitoneal injection, and vaccines containing recombinant flagellin and envelope domain III fusion proteins were administered via intramuscular injection. All vaccines were prepared as a dosage form of 200 µl using phosphate buffered saline (hereinafter referred to as PBS; 137 mM sodium chloride, 2.7 mM potassium chloride, 4.3 mM sodium hydrogen phosphate, and 1.4 mM potassium dihydrogen phosphate dissolved in deionized water, pH 7.4) as the diluent.

Sodium Dodecyl Sulfate Polyacrylamide Gel Electrophoresis (SDS-PAGE)

SDS-PAGE was performed as follows. In brief, protein samples were mixed with SDS-loading buffer (50 mM Tris-HCl (pH 6.8), 100 mM dithiothreitol (DTT), 2% SDS, 0.1% bromophenol blue, and 10% glycerol) at a volume ratio of 3:1 and boiled for 5 minutes. At the same time, gels for electrophoresis with a 12% separating gel (2.5 ml of 1 M Tris (pH 8.8), 3.3 ml deionized water, 4 ml of 30% acrylamide mix, 0.1 ml of 10% SDS, 0.1 ml of 10% ammonium persulfate (APS), and 0.01 ml TEMED) and a 5% stacking gel (0.63 ml of 1 M Tris (pH 6.8), 3.4 ml deionized water, 0.83 ml of 30% acrylamide mix, 0.05 ml of 10% SDS, 0.05 ml of 10% APS, and 0.005 ml TEMED) were casted. Electrophoresis was performed at 80V for stacking and at 150V for separating. Gels were then stained in coomassie blue staining solution (0.1% coomassie R250, 10% acetic acid, and 50% methanol) for 1 hour and destained with destaining solution (10% acetic acid and 30% methanol).

Western Blotting

Western blotting was performed as follows. In brief, protein samples separated on SDS-PAGE gel were transferred to a nitrocellulose membrane at 135V. The membrane was then incubated in Tris-buffered saline with Tween-20 (hereinafter referred to as TBST; 50 mM Tris, 150 mM sodium chloride, and 0.05% Tween-20) containing 5% skimmed milk to block the nonspecific binding for at least 1 hour with shaking. After washed three times with TBST, the membrane was treated with anti-prM antibody (ATCC® HB114™) or anti-DI/DII antibody (ATCC® HB112™) at a dilution factor of 1:100 in TBST for 1 hour. After washed three times with TBST, the membrane was treated with horseradish peroxidase (HRP)-conjugated anti-mouse IgG secondary antibody (GeneTex) at a dilution factor of 1:1500 in TBST for 1 hour, and washed three times with TBST. For detection, an enhanced chemiluminescence reagent (Western Lighting Plus ECL, PerkinElmer) was added to the membrane to produce luminescence signals, which was visualized on the Medical X-ray Film (Fujifilm).

Example 1

Preparation of the Live-Attenuated Dengue Viruses

This example exemplifies methods of preparing the live-attenuated dengue virus and the live-attenuated chimeric dengue virus for the first vaccine of the vaccine combination against multiple dengue virus serotypes of the present invention. In one preferable embodiment of the present invention, the live-attenuated dengue virus DENV4 Δ30 was obtained from a mutation-containing plasmid of the infectious dengue virus type 4 clone 2A (DENV4-2A), which contained the full-length cDNA of DENV4 strain 814669 and a deletion mutation of 30 nucleotides at the 3' noncoding region. Moreover, this DENV4 Δ30 plasmid along with a plasmid of a chimeric dengue virus DENV2/4 were used to prepare the live-attenuated type 2/type 4 chimeric dengue virus DENV2/4 Δ30 of the preset invention. The DENV4 Δ30 plasmid and the DENV2/4 plasmid were both provided by the US National Institute of Health. The chimeric DENV2/4 plasmid had the prM and E genes of DENV2-NGC substituted for those genes of DENV4-2A. For preparation of the plasmid of DENV2/4 Δ30, the Cla I-Xho I fragment of the DENV4 Δ30 plasmid was replaced with that of the DENV2/4 plasmid. The nucleotide sequence of the DENV2/4 Δ30 plasmid was verified by sequence analysis.

The method of preparing the live-attenuated dengue virus DENV4 Δ30 and the live-attenuated chimeric dengue virus DENV2/4 Δ30 from the DENV4 Δ30 plasmid and the DENV2/4 Δ30 plasmid was described as follows. First, to carry out in vitro transcription, the abovementioned plasmids were linearized by cleavage with Kpn I restriction enzyme and then transcribed to produce the RNA transcripts of DENV4 Δ30 and DENV2/4 Δ30 using RiboMAX large scale RNA production system (Promega) containing SP6 RNA polymerase. The 5' ends of the RNA transcripts were further capped with a protective oligoribonucleotide m7G (5')ppp(5')G using Script Cap Capping enzyme (EPICENTRE). The capped RNA transcripts were purified with RNA isolation reagent TRIzol LS (Invitrogen) according to manufacturer's instructions. Next, the purified RNA transcripts were transfected into Vero cells with cell transfection reagent DMRIE-C (Invitrogen) according to manufacturer's instructions. After incubation of the transfected Vero cells at 37° C. for 5-7 days, the DENV4 Δ30 and DENV2/4 Δ30 viruses were harvested by collecting the culture supernatants. To obtain virus stocks with higher virus titer, the viruses were passaged several times in Vero cells infected with the culture supernatants. The virus stocks were stored at −80° C.

To examine the infectivity of the DENV4 Δ30 and DENV2/4 Δ30 viruses obtained based on this method, focus forming assay was performed to determine the focus forming unit (FFU) in monolayer Vero E6 cells infected with these two viruses. First, Vero cells seeded at the density of $10^5$ cells/well in 24-well plates (37° C.) were infected with the DENV4 Δ30 or DENV2/4 Δ30 virus at a multiplicity of infection (MOI) of 1. The culture supernatants were collected daily by centrifugation (3000 rpm, 15 minutes, 4° C.). Next, Vero E6 cells were seeded at the density of $5\times10^5$ cells/well in 6-well plates and incubated at 37° C. for one day. The 10-fold serially diluted culture supernatants mentioned above were added to each well for an hour of incubation at 37° C., and 4 ml/well of MEM medium containing 1.1% methylcellulose (Sigma) and 100 U/ml penicillin and streptomycin was added to the 6-well plates for 5-7 days of incubation at 37° C. with 5% $CO_2$. The cells were then fixed for at least 1 hour by adding 4% paraformaldehyde. The cells were washed three times with PBS containing 0.05% Tween-20 (hereinafter referred to as PBST), and treated with dengue virus monoclonal antibody 2H2, which was expressed by and purified from the ATCC HB-114 hybridoma cells, at a dilution factor of 1:300 for 1 hour. After washed three times with PBST, the cells were treated with HRP-conjugated goat anti-mouse IgG secondary antibody (GeneTex) at a dilution factor of 1:1500 for 1 hour, and washed three times with PBST. For visualization and determination of the focus forming units, the cells were stained for 20 minutes with the diaminobenzidine (DAB) kit (Invitrogen), and the reaction was stopped by washing with water.

Figure 1B:
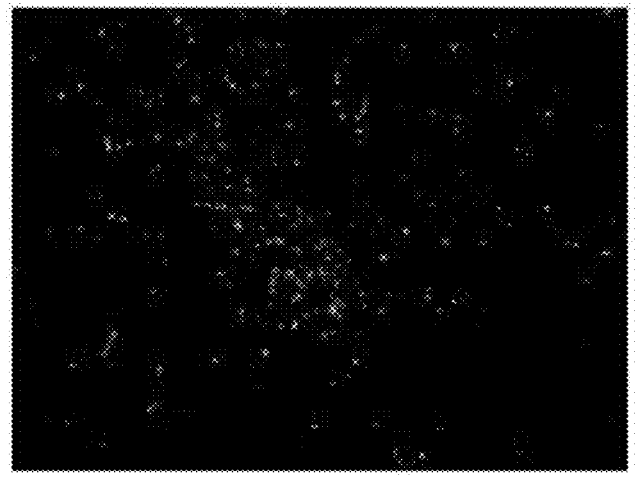
Figure 1C:
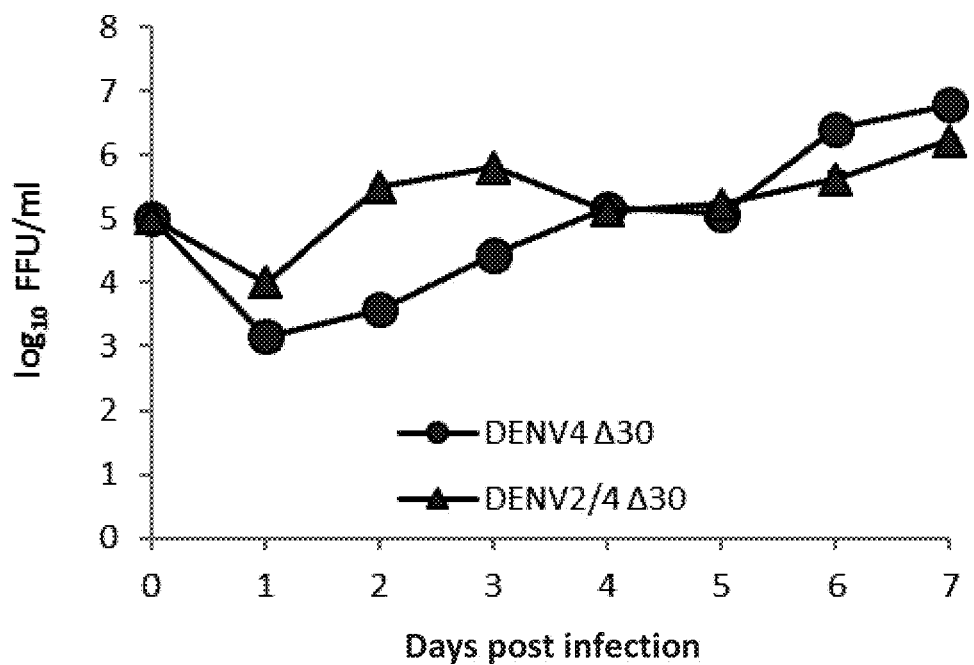
FIG. 1C shows virus replication curves for the live-attenuated dengue virus DENV4 Δ30 and the live-attenuated chimeric dengue virus DENV2/4 Δ30 in Vero E6 cells.

FIGS. 1A-1B are micrographs (IX70, Olympus, magnification 200×) of the Vero E6 cells at 6 days post-infection in the focus forming assay. It showed that both the live-attenuated dengue virus DENV4 Δ30 and the live-attenuated chimeric dengue virus DENV2/4 Δ30 used in the vaccine combination of the present invention caused cytopathic effects. FIG. 1C shows virus replication curves, demonstrating that both the live-attenuated dengue virus DENV4 Δ30 and the live-attenuated chimeric dengue virus DENV2/4 Δ30 reached a virus titer of $10^6$ FFU/ml. These results indicate that both of the viruses are capable of replicating in Vero cells and may be employed in the vaccine combination of the present invention.

Example 2

Preparation of the Recombinant Flagellin and Envelope Domain III Fusion Proteins This example illustrates methods of preparing the recombinant flagellin and envelope domain III fusion proteins for the second vaccine of the vaccine combination against multiple dengue virus serotypes of the present invention. The envelope domain III (DIII) of the recombinant flagellin and envelope domain III (FliC-DIII) fusion protein is derived from either one of dengue virus serotypes 1, 2, 3, and 4. It is the third domain of the envelope protein, which participates in binding of dengue virus to host cell receptors, and it has a molecular weight of about 13 kDa. Flagellin (abbreviated as FliC) is derived from *Salmonella typhimurium*. It activates Toll-like receptor-5 (TLR5) and elicits primary immune response. For preparation of the recombinant FliC-DIII fusion proteins, DNA constructs containing the FliC gene and the DIII gene fragment from the 5' end to the 3' end were first prepared. The two genes could be linked by a deoxyribonucleotide encoding an amino acid linker of four repeats of glycine and serine (GS4 linker). The DIII gene fragment was derived from dengue virus type 1, type 2, type 3, or type 4. Among them, the dengue virus type 1 was DENV1-Hawaii, the dengue virus type 2 was DENV2-NGC, the dengue virus type 3 was DENV3-H87, and the dengue virus type 4 was DENV4-2A. Next, each of the abovementioned DNA constructs was cloned into a protein expression vector pET-22b(+) (Norvagen), causing the recombinant FliC-DIII fusion protein to be expressed with a hexahistidine tag (His-tag) at the C-terminus. A DNA construct containing only the FliC gene or the DIII gene fragment was also cloned into the abovementioned protein expression vector for the following experiments.

For expression of the recombinant FliC-DIII fusion proteins, *E. coli* BL21 (DE3) (Invitrogen) was transformed with either one of the protein expression vectors carrying the DNA constructs previously described and cultured at 37° C. overnight in LB broth containing 100 μg/ml ampicillin. The overnight culture was inoculated at 1% (v/v) into LB broth without antibiotics and incubated at 37° C. until the absorbance at 600 nm (OD600) reached approximately 0.6. The expression of the recombinant fusion proteins were induced by addition of 1 mM isopropyl β-D-1-thiogalactopyranoside (IPTG) and further incubation at 37° C. for 4-6 hours. The culture media were then centrifuged (5000 rpm, 15 minutes, 4° C.) to collect the cell pellets. The recombinant FliC and the recombinant DIII proteins were also expressed for the following experiments according to the same method.

The abovementioned cell pellets were resuspended in buffer A (300 mM Tris, 500 mM sodium chloride, 10 mM imidazole, 5% glycerol, pH 7.4) containing 1 mM phynelmethane-sulfonyl fluoride (PMSF) and disrupted by high pressure homogenization (15 Kpsi). Since the recombinant FliC-DIII fusion proteins were present in inclusion bodies, the crude extracts of the recombinant FliC-DIII fusion proteins were obtained by centrifugation of the cell lysates at 10,000 rpm for 10 minutes at 4° C. to yield the inclusion bodies which were then solubilized in buffer A containing 8 M urea. The crude extracts of the recombinant DIII proteins were prepared for the following experiments according to the same method, while the recombinant FliC was present in the supernatant of the cell lysates.

For protein purification, the crude extracts of the recombinant FliC-DIII fusion proteins were loaded onto a nickel-chelating affinity column comprising 8 ml of Ni-NTA resin (TOSOH), washed with 30 ml of buffer A containing 0.5% Triton X-100, and eluted with 30-40% buffer B (300 mM Tris, 50 mM sodium chloride, 500 mM imidazole, 5% glycerol, pH 7.4). The purified fractions of the recombinant FliC-DIII fusion proteins were concentrated in PBS using Amicon 10K filter unit (Merck Millipore) and stored at −20° C. The recombinant FliC and the recombinant DIII proteins were purified for the following experiments according to the same method.

Figure 2A:
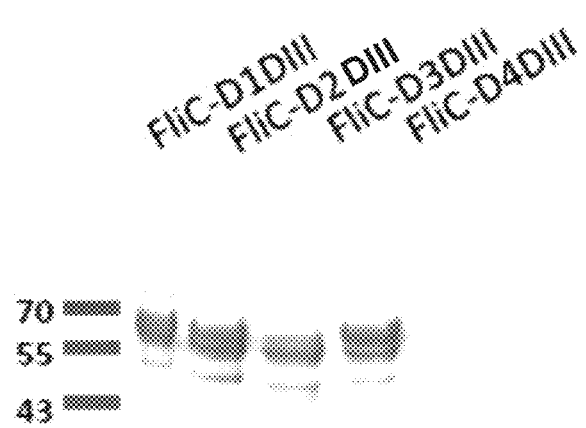
FIG. 2A shows an image of sodium dodecyl sulfate polyacrylamide gel electrophoresis (SDS-PAGE) for analyzing the purity of a recombinant flagellin-dengue virus type 1 envelope domain III fusion protein, a recombinant flagellin-dengue virus type 2 envelope domain III fusion protein, a recombinant flagellin-dengue virus type 3 envelope domain III fusion protein, and a recombinant flagellin-dengue virus type 4 envelope domain III fusion protein of the present invention, which are denoted as FliC-D1DIII, FliC-D2DIII, FliC-D3DIII, and FliC-D4DIII, respectively.
Figure 2B:
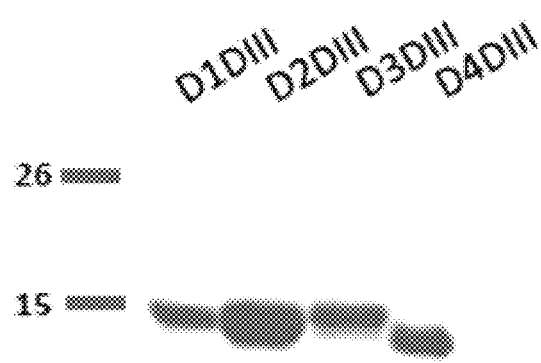
FIG. 2B shows an image of SDS-PAGE for analyzing the purity of recombinant envelope domain III proteins of dengue virus type 1, type 2, type 3, and type 4, which were denoted as D1DIII, D2DIII, D3DIII, and D4DIII, respectively.

The purity of the recombinant FliC-DIII fusion proteins or the recombinant DIII proteins was verified by SDS-PAGE. As shown in FIG. 2A, a single major band of about 64 kDa was observed for each of the recombinant flagellin-dengue virus type 1 envelope domain III fusion protein, the recombinant flagellin-dengue virus type 2 envelope domain III fusion protein, the recombinant flagellin-dengue virus type 3 envelope domain III fusion protein, and the recombinant flagellin-dengue virus type 4 envelope domain III fusion protein, which were denoted as FliC-D1DIII, FliC-D2DIII, FliC-D3DIII, and FliC-D4DIII, respectively. As shown FIG. 2B, a single major band of about 13 kDa was observed for each of the recombinant DIII proteins of dengue virus type 1, type 2, type 3, and type 4, which were denoted as D1DIII, D2DIII, D3DIII, and D4DIII, respectively. The results reveal that the four types of recombinant FliC-DIII fusion proteins or the four types of recombinant DIII proteins can be prepared with high purity based on the method previously described.

Figure 3:
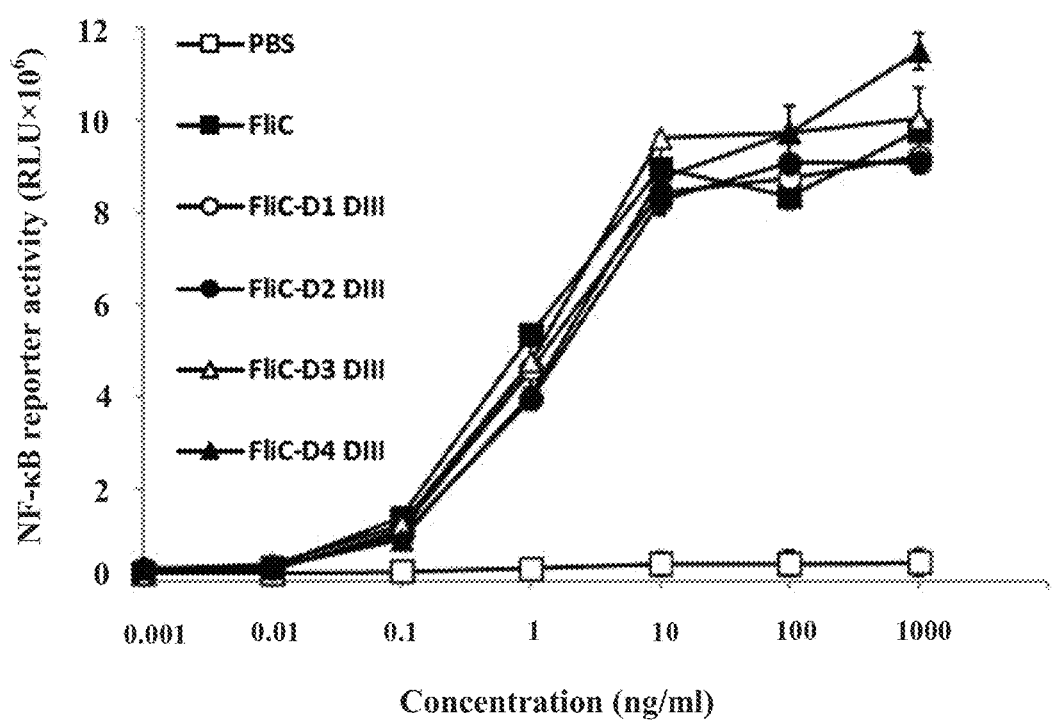
FIG. 3 shows NF-κB reporter activities for analyzing stimulation of the TLR5 signaling pathway by the recombinant fusion proteins FliC-D1DIII, FliC-D2DIII, FliC-D3DIII, and FliC-D4DIII.

Since FliC is the ligand of TLR5, TLR5-dependent functional assay was performed as follows to examine the ability of the abovementioned four types of recombinant FliC-DIII fusion proteins to stimulate the TLR5 signaling pathway. First, 293A cells at the number of $10^7$ were cultured in a 10 cm culture dish for one day (37° C., 5% $CO_2$) and co-transected with 7.5 μg of pUNO1-hTLR5 plasmid (Invivo-Gen) and 5.5 μg of pGL4.32 [luc2p/NF-κB-RE/Hygro] plasmid (Promega) by using Turbofect transfection reagent (Fermentas). These two plasmids are an expression plasmid of TLR5 and a reporter plasmid of NF-κB, which is a transcription factor in downstream TLR5 signaling pathway. The NF-κB reporter plasmid would express luciferase once the TLR5 expressed in cells is stimulated by ligands. The transfected cells, at the next day, were seeded at the density of $5 \times 10^4$ cells/well in a 96-well plate, followed by addition of a 10-fold serial dilution of the recombinant FliC protein or the recombinant FliC-DIII fusion protein of dengue virus type 1, type 2, type 3, or type 4, each of which was first diluted to 1 μg/ml in DMEM medium. After incubation at 37° C. for 5 hours, the cells were disrupted and treated with the luciferase substrate (neolite assay, PerkinElmer). After 5 minutes, VICTOR3 Multi-labeled Microplate Reader (PerkinElmer) was used to read the 96-well plate for measurement of the relative luminescence units (RLU) at 560 nm. The results of the NF-κB reporter activity assay were shown in FIG. 3. The addition of the recombinant FliC, as the positive control group, led to a luminescence value of $10^7$ RLU, indicating capability of this protein to stimulate the TLR5 signaling pathway. Also, the recombinant FliC-DIII fusion proteins of dengue virus type 1, type 2, type 3, or type 4 of the present invention resulted in similar relative luminescence values, indicating that the FliC domain of these recombinant FliC-DIII fusion proteins was functional and able to elicit the TLR5 signaling pathway.

Example 3

Preparation of the Adenoviral Vectors Expressing Precursor Membrane (prM) Protein and Envelope (E) Protein This example illustrates methods of preparing the adenoviral vectors expressing prM protein and E protein (both proteins collectively referred to as prME) of dengue virus serotypes 1, 2, 3, and 4 for the vaccine combination against multiple dengue virus serotypes of the present invention. First, a gene fragment containing prM and E genes of each dengue virus serotype was amplified by polymerase chain reaction (PCR) using cDNA containing the prME gene fragment of dengue virus type 1, type 2, type 3, or type 4 and specific primers. After DNA sequence determination (Biosune OptimumGene™), the codon-optimized gene fragments were synthesized and PCR amplified. Each of the amplified gene fragments was first inserted into the transfer vector pENTR™ (Invitrogen) separately, and then cloned to the adenoviral plasmid pAd/CMV/V5-DEST™ (Invitrogen) using LR Clonase™ II Enzyme Mix (Invitrogen) to generate the adenoviral plasmid expressing prM and E proteins of dengue virus type 1, type 2, type 3, or type 4.

To obtain adenovirus particles used as the adenoviral vectors for the vaccine combination, the abovementioned four types of adenoviral plasmids were cleaved with Pac I restriction enzyme to expose the inverted terminal repeats (ITR), and then transfected into 293A cells separately using Turbofect transfection reagent (Fermentas). The transfected cells and culture media were collected after incubation at 37° C. for about 10-15 days when the cytopathic effects were obvious. The cells were disrupted by freeze-thaw twice to release the intracellular viral particles, and the supernatants of the cell lysates were collected by centrifugation (3000 rpm, 15 minutes, 4° C.) to obtain the adenoviral vector expressing prM and E proteins of dengue virus type 1, type 2, type 3, or type 4, referred to as Ad-D1 prME, Ad-D2 prME, Ad-D3 prME, and Ad-D4 prME, respectively. The viral stocks were stored at −80° C.

Figure 4A:
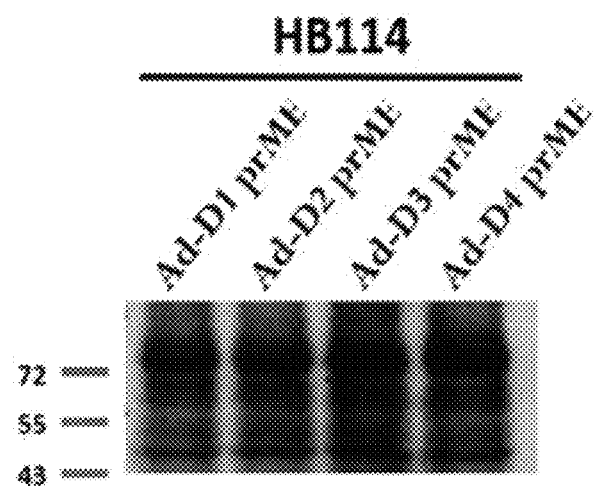
FIG. 4A shows detection of precursor membrane proteins of dengue virus type 1, type 2, type 3, and type 4 expressed by the corresponding four types of adenoviral vectors, namely Ad-D1 prME, Ad-D2 prME, Ad-D3 prME, and Ad-D4 prME, respectively, by Western blotting analysis.
Figure 4B:
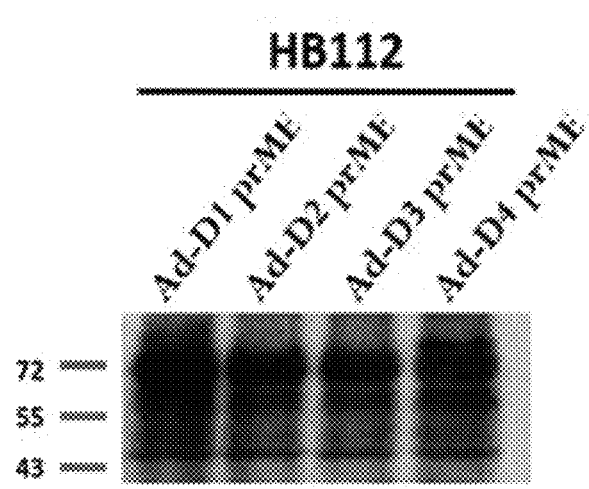
FIG. 4B shows detection of envelope proteins of dengue virus type 1, type 2, type 3, and type 4 expressed by the corresponding four types of adenoviral vectors, namely Ad-D1 prME, Ad-D2 prME, Ad-D3 prME, and Ad-D4 prME, respectively, by Western blotting analysis.
Figure 5A:
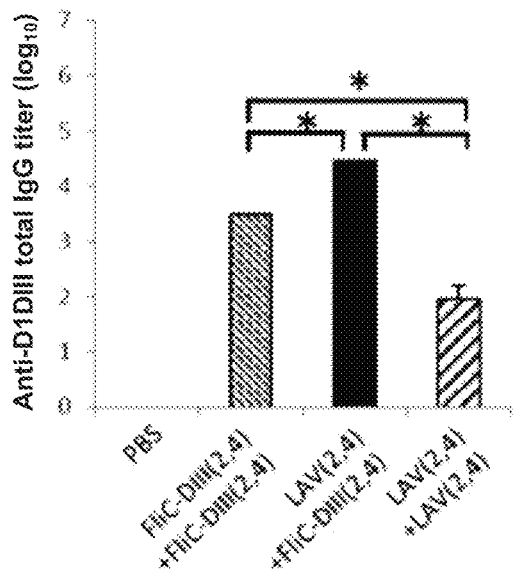
FIGS. 5A-5D show total serum immunoglobulin G (IgG) titers determined by enzyme-linked immunosorbent assay (ELISA) against recombinant envelope domain III protein of dengue virus type 1, type 2, type 3, or type 4 for AG129 mice receiving different immunizations.
Figure 5B:
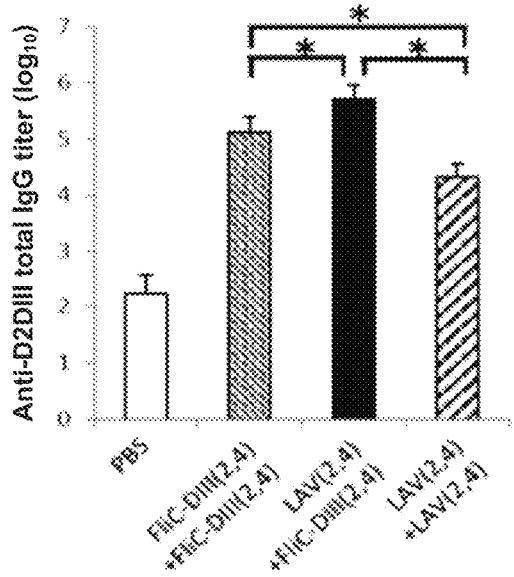
Figure 5C:
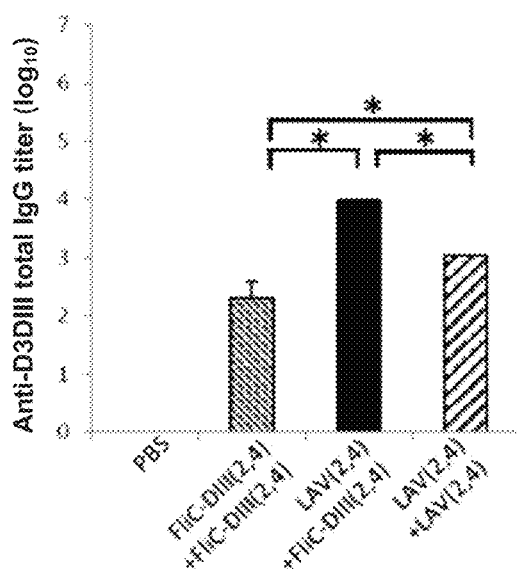
Figure 5D:
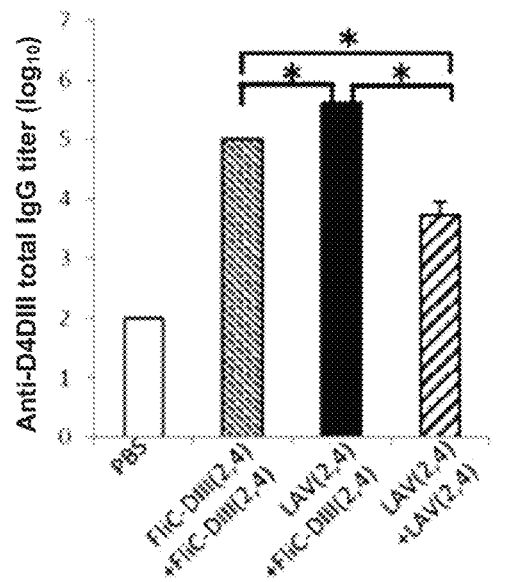
Figure 6A:
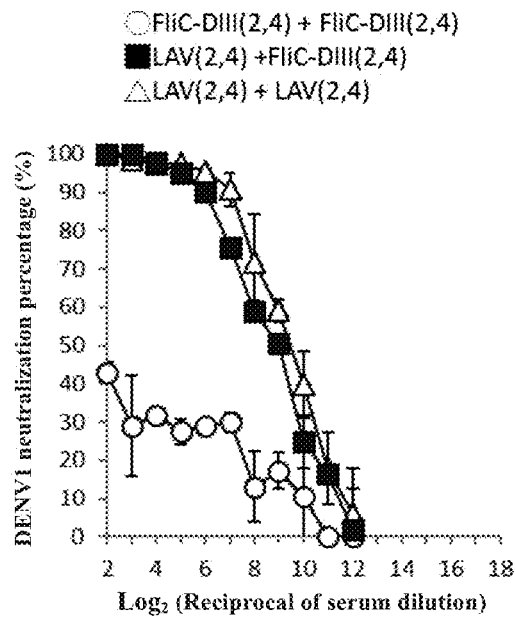
FIGS. 6A-6D show neutralization curves determined by focus reduction neutralizing test (FRNT) for serum neutralizing antibodies against dengue virus type 1, type 2, type 3, or type 4 in AG129 mice received different immunizations.
Figure 6B:
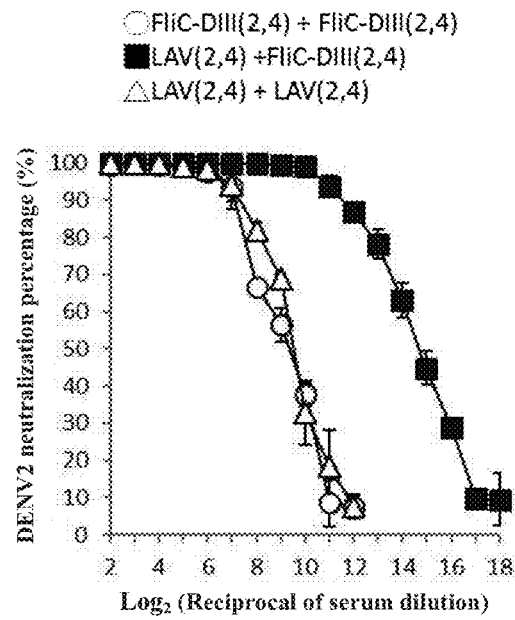
Figure 6C:
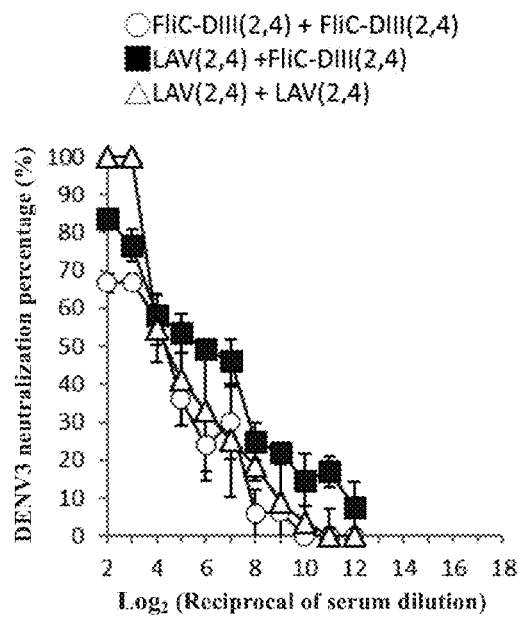
Figure 6D:
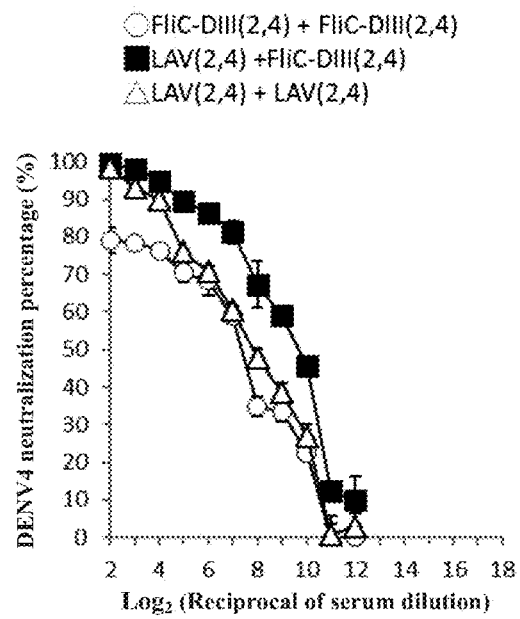
Figure 7A:
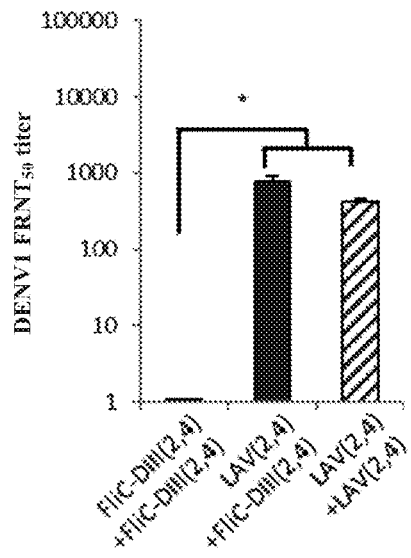
FIGS. 7A-7D show serum neutralizing antibody titers, calculated based on FIGS. 6A-6D, against dengue virus type 1, type 2, type 3, or type 4 for the AG129 mice receiving different immunizations.
Figure 7B:
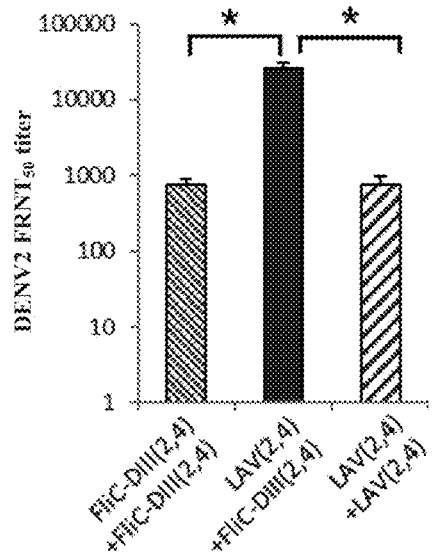
Figure 7C:
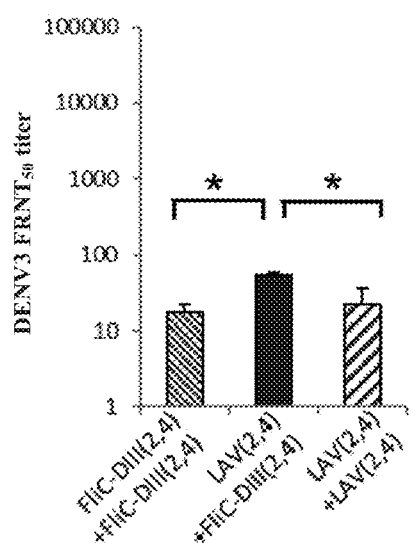
Figure 7D:
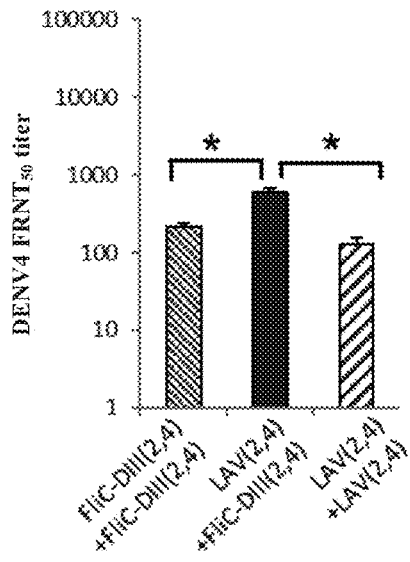

The prM protein and E protein expressed by the abovementioned four types of adenoviral vectors were verified by Western blotting. Because the prM and E proteins could be detected within 24 hours post-transfection of the 293A cells previously described, the samples for Western blotting analysis were collected from the cell lysates within 24 hours post-transfection. As shown in FIG. 4A, the expressed prM proteins of dengue virus type 1, type 2, type 3, and type 4 were detected for the corresponding four types of adenoviral vectors using anti-prM antibody ATCC® HB-114™ and the signals were observed at about 72 kDa. As shown in FIG. 4B, the expressed E proteins of dengue virus type 1, type 2, type 3, and type 4 were detected for the corresponding four types of adenoviral vectors using anti-DI/DII antibody ATCC® HB112™ and the signals were observed at about 72 kDa. The results indicate that the adenoviral vectors expressing dengue virus prM and E proteins can be prepared based on the method previously described When the abovementioned adenoviral vectors were employed in the vaccine combination, the adenovirus titers were determined by plaque assay, measuring the plaque forming units (PFU) in monolayer 293A cells infected with the four adenoviruses. For the assay, 293A cells were seeded in 6-well plates and incubated at 37° C. for one day to reach the cell density of $10^6$ cells/well. The 10-fold serially diluted adenoviruses mentioned above were then added to each well for an overnight incubation at 37° C. Next, the media containing the diluted adenoviruses were removed and 2 ml/well of DMEM medium containing 1% agarose and 100 U/ml penicillin and streptomycin was added to the 6-well plates for 2 days of incubation at 37° C., followed by addition of 1 ml DMEM medium per well. The plaques were visibly quantified 8-10 days after the cells were infected with adenoviruses and plaque forming units was reported.

Example 4

A Vaccine Combination Including a Divalent First Vaccine Containing the Live-Attenuated Dengue Viruses and a Divalent Second Vaccine Containing the Recombinant Flagellin and Envelope Domain III Fusion Proteins 4.1 Assessment of Total Immunoglobulin G (IgG) Titers Against Recombinant Envelope Domain III Proteins To examine the efficacy of the vaccine combination of the present invention to elicit general immune responses against multiple dengue virus serotypes in a subject, total serum IgG titers against recombinant DIII proteins were first evaluated in this example after AG129 mice were injected, based on either homologous or heterologous prime-boost immunization strategies, with the live-attenuated dengue virus DENV4 Δ30 and the live-attenuated chimeric dengue virus DENV2/4 Δ30, or the recombinant FliC-DIII fusion proteins of dengue virus type 2 and type 4, or the combination of the abovementioned two items. TABLE 1 shows different immunization regimens for mice, including (a) two doses of the recombinant fusion proteins FliC-D2DIII and FliC-D4DIII (denoted as FliC-DIII (2,4)+FliC-DIII(2,4)); (b) priming with the DENV2/4 Δ30 and DENV4 Δ30 viruses followed by boosting with the recombinant fusion proteins FliC-D2DIII and FliC-D4DIII (denoted as LAV(2,4)+FliC-DIII(2,4)), wherein the DENV2/4 Δ30 virus and the DENV4 Δ30 virus were mixed at a number ratio of 2:1 to 1:2, and they were mixed at 1:1 in one embodiment of the present invention; (c) two doses of the DENV2/4 Δ30 and DENV4 Δ30 viruses (denoted as LAV(2,4)+LAV(2,4)). The time interval between the prime and boost immunizations for each immunization regimen was about 1-5 weeks. In one preferred embodiment, the time interval was 3 weeks. Blood samples were collected from the mice two weeks after the boost immunization. The blood samples were centrifuged at 3000 rpm for 15 minutes to isolate the serum from the blood cells, and the serum was inactivated by heating at 56° C. for 30 minutes and stored at −20° C.

TABLE 1

| Formulations | Prime | Boost |
| --- | --- | --- |
| FliC-DIII(2,4) + FliC-DIII(2,4) | FliC-D2DIII 20 μg/mouse FliC-D4DIII 20 μg/mouse | FliC-D2DIII 20 μg/mouse FliC-D4DIII 20 μg/mouse |
| LAV(2,4) + FliC-DIII(2,4) | DENV2/4 Δ30 $10^4$ FFU/mouse DENV4 Δ30 $10^4$ FFU/mouse | FliC-D2DIII 20 μg/mouse FliC-D4DIII 20 μg/mouse |
| LAV(2,4) + LAV(2,4) | DENV2/4 Δ30 $10^4$ FFU/mouse DENV4 Δ30 $10^4$ FFU/mouse | DENV2/4 Δ30 $10^4$ FFU/mouse DENV4 Δ30 $10^4$ FFU/mouse |

Total serum IgG titers against the recombinant DIII proteins of dengue virus type 1, 2, 3, and 4 were determined by enzyme-linked immunosorbent assay (ELISA). First, the ELISA plate was coated with 0.2 μg of the recombinant DIII proteins in 0.05M carbonate buffer and incubated at 4° C. overnight. After washed with PBST three times, each well of the plate was blocked with 150 μl of 1% bovine serum albumin (BSA) in PBS at 37° C. for 2 hours to prevent nonspecific biding, and then washed with 100 μl PBST. Next, the mouse sera were 4-fold serially diluted from a dilution factor of 1:100 with dilution buffer (PBS containing 1% BSA and 0.05% Tween 20) and added to the ELISA plate for an hour of incubation at room temperature. After washed with PBST 3 times, each well of the ELISA plate was treated with 100 μl HRP-conjugated goat anti-mouse IgG antibody at a dilution factor of 1:10000 at room temperature for 1 hour, and washed with PBST three times. Finally, 100 μl/well of 3,3',5,5'-tetramethylbenzidine (TMB)(BioLegend), the substrate of HRP, was added to the ELISA plate for coloration reaction in the dark for 15 minutes, and the reaction was stopped by addition of 2 N sulfuric acid. The absorbance at 450 nm was measured with an ELISA reader (DYNEX MRX II) for each well. The end-point titers of total IgG were defined as the maximal serum dilution that produced an OD value of over 0.2.

After the mice were immunized with the three formulations according to TABLE 1, total serum IgG titers against the recombinant DIII protein of dengue virus type 1, type 2, type 3, or type 4 were determined and shown in FIGS. 5A-5D. In each of the figures, treatment with PBS serves as the control group, and * represents p<0.05. According to FIGS. 5A-5D, when compared with the homologous prime-boost immunization, the heterologous prime-boost immunization of mice with a first vaccine containing the DENV2/4 Δ30 and DENV4 Δ30 viruses followed by a second vaccine containing the recombinant fusion proteins FliC-D2DIII and FliC-D4DIII elicited the highest total serum IgG titers against the four types of recombinant DIII proteins, including a titer of 29160 against D1DIII, a titer of 614400 against D2DIII, a titer of 9720 against D3DIII, and a titer of 409600 against D4DIII. These data showed that the highest titers were against the recombinant DIII proteins of dengue virus type 2 and type 4.

4.2 Assessment of Neutralizing Antibody Titers Against Dengue Virus

Serum neutralizing antibody titers against dengue virus were further compared in this example by focus reduction neutralizing test (FRNT) after AG129 mice were immunized with the three formulations according to TABLE 1. The mouse sera were 2-fold serially diluted from a dilution factor of 1:4 in Hank's balanced salt solution and incubated with 200 FFU dengue virus type 1, type 2, type 3, or type 4 at 37° C. for 1 hour. The dengue virus type 1 was DENV1-Hawaii, the dengue virus type 2 was DENV2-NGC, the dengue virus type 3 was DENV3-H87, and the dengue virus type 4 was DENV4-2A. Next, the sera-virus mixtures were added to 6-well plates seeded with monolayer Vero E6 cells for determination of FFU by focus forming assay. A reduction in focus number was used to calculate the neutralization percentage and to plot the neutralization curves. The neutralizing antibody titer, represented by $FRNT_{50}$, was defined as the maximal serum dilution that caused over 50% reduction in focus number and was determined by regression analysis using the software Graph Pad Prism version 6.

The neutralization curves for mouse serum neutralizing antibodies against dengue virus type 1, type 2, type 3, or type 4 were shown in FIGS. 6A-6D. The neutralizing antibody titers calculated based on FIGS. 6A-6D were shown in FIGS. 7A-7D, in which * represents p<0.05. According to FIGS. 6A-6D, when compared with the homologous prime-boost immunization, the heterologous prime-boost immunization of mice with a first vaccine containing the DENV2/4 Δ30 and DENV4 Δ30 viruses followed by a second vaccine containing the recombinant fusion proteins FliC-D2DIII and FliC-D4DIII elicited the higher titers of serum neutralizing antibodies against the four dengue virus serotypes. FIGS. 7A-7D particularly shows that the abovementioned heterologous prime-boost immunization elicited high titers of mouse serum neutralizing antibodies against dengue virus type 1, type 2, and type 4, including a titer of 772 against DENV1, a titer of 12899 against DENV2, and a titer of 595 against DENV4. The highest neutralizing antibody titer was against dengue virus type 2. These results are matched with those of the assessment of total IgG titers against recombinant DIII proteins, indicating that the antibodies specific for envelope domain III are the major contributors to the ability of the DENY-neutralizing antibodies to neutralize dengue virus.

4.3 Protection of Antisera Against Dengue Virus

Sucking mice assay was performed in this example to further examine the passive protection against viral infection in sucking mice due to dengue virus neutralization by the antisera from AG129 mice immunized with the three formulations according to TABLE 1. First, the heat-inactivated AG129 mouse sera were mixed with $10^4$ FFU dengue virus type 2 or type 4 at a ratio of 1:1 to a final volume of 30 μl and incubated at 37° C. for 1 hour. The dengue virus type 2 was DENV2-NGC and the dengue virus type 4 was DENV4-2A. The sera-virus mixtures were then injected intracranially into one-day-old suckling 129 mice. The survival of the suckling mice was recorded daily for survival rate calculation.

Figure 8A:
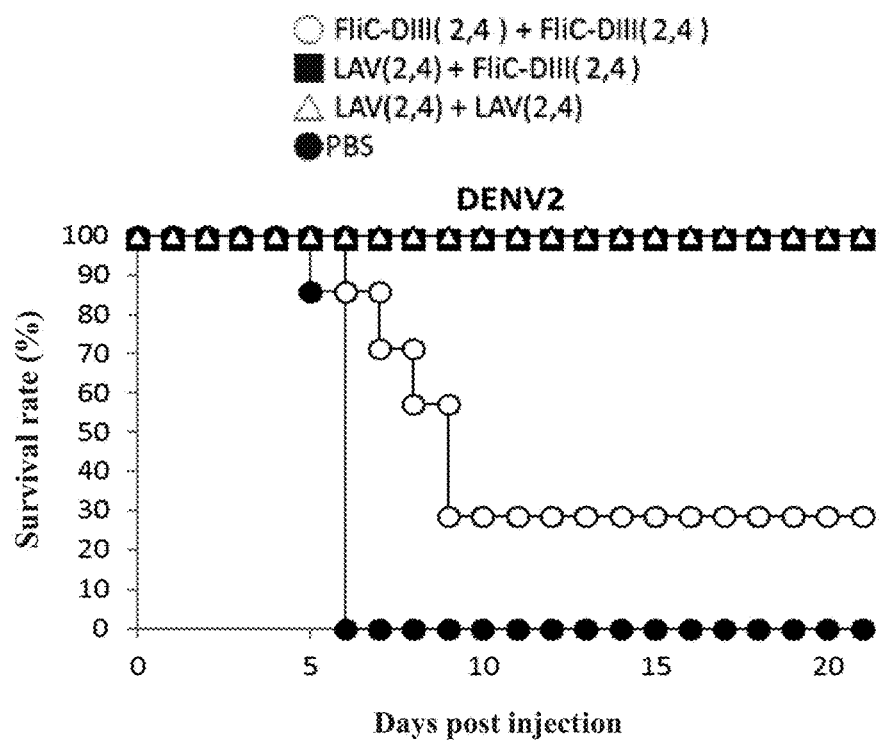
FIGS. 8A-8B show survival curves for 129 suckling mice injected with dengue virus type 2 or type 4 that was neutralized by different antisera.
Figure 8B:
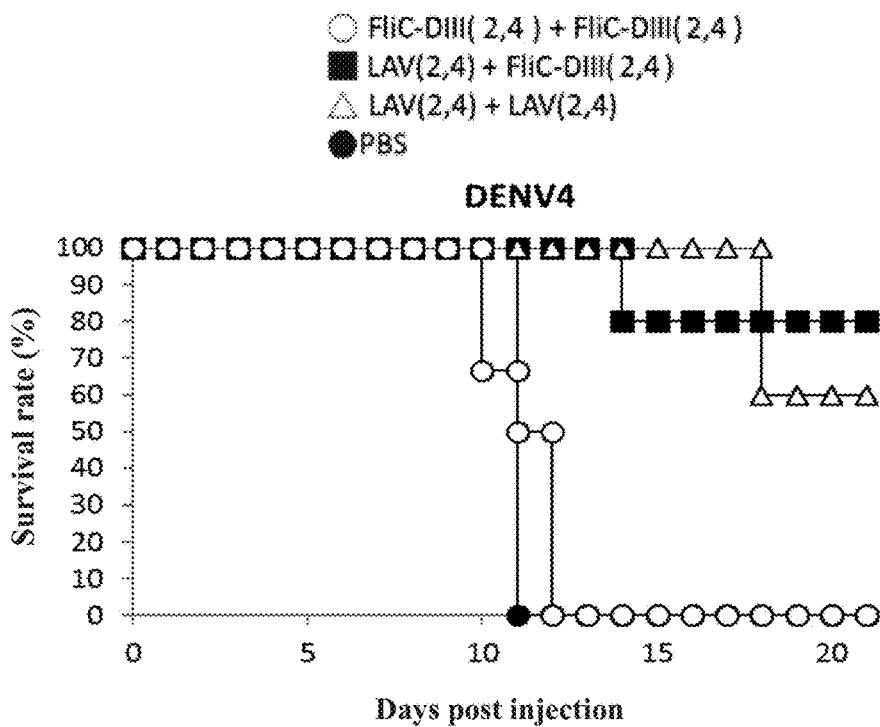
Figure 9A:
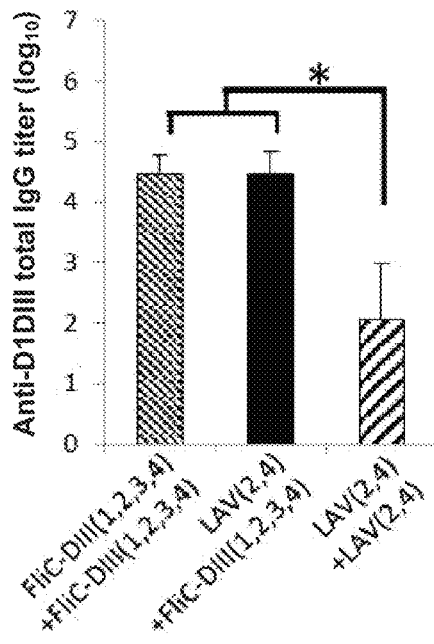
FIGS. 9A-9D show total serum IgG titers determined by ELISA against recombinant envelope domain III protein of dengue virus type 1, type 2, type 3, or type 4 for AG129 mice receiving different immunizations.
Figure 9B:
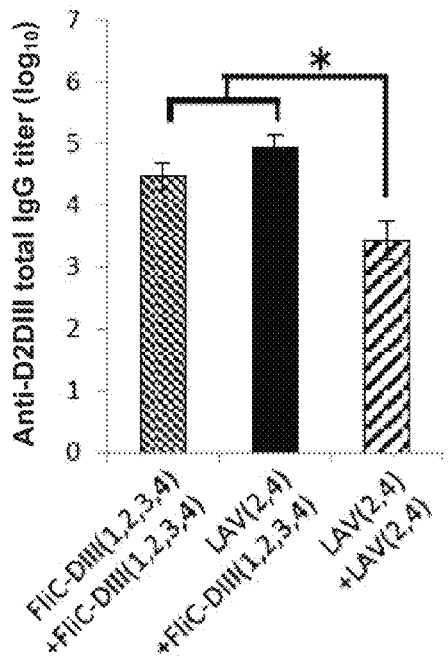
Figure 9C:
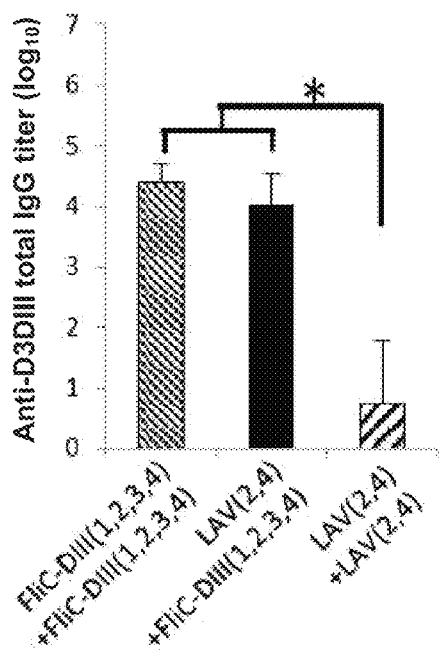
Figure 9D:
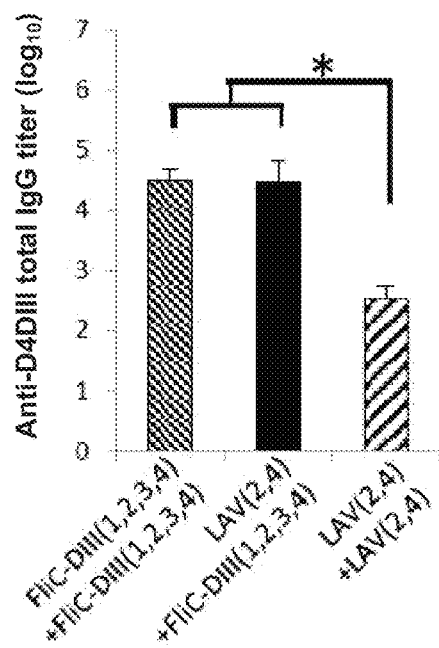
Figure 10A:
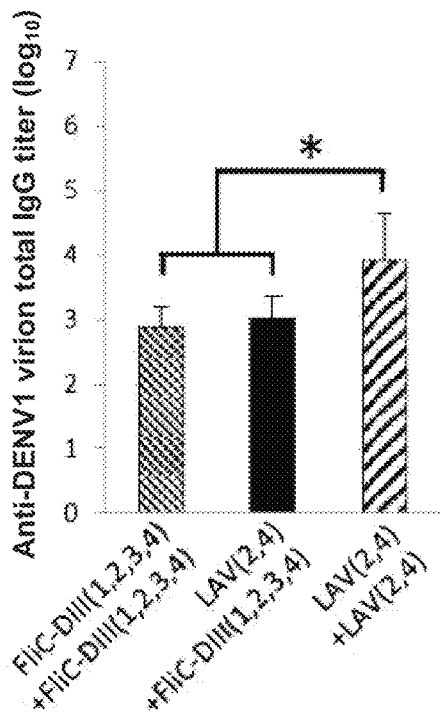
FIGS. 10A-10D show total serum IgG titers determined by ELISA against virions of dengue virus type 1, type 2, type 3, or type 4 for AG129 mice receiving different immunizations.
Figure 10B:
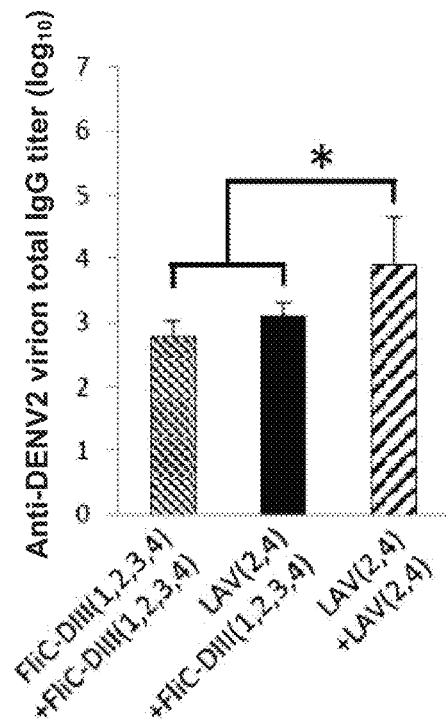
Figure 10C:
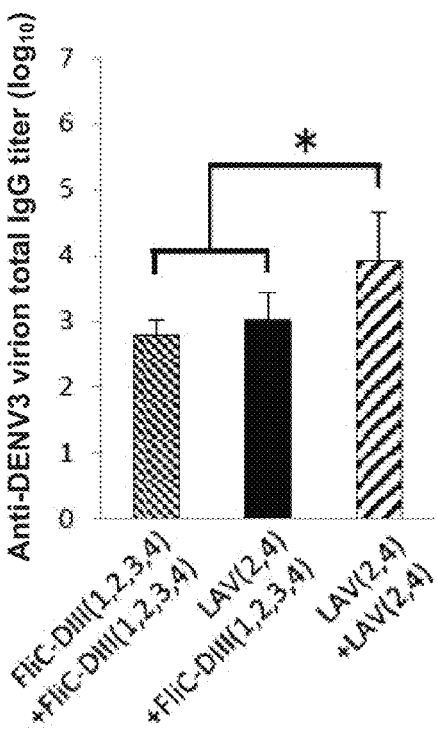
Figure 10D:
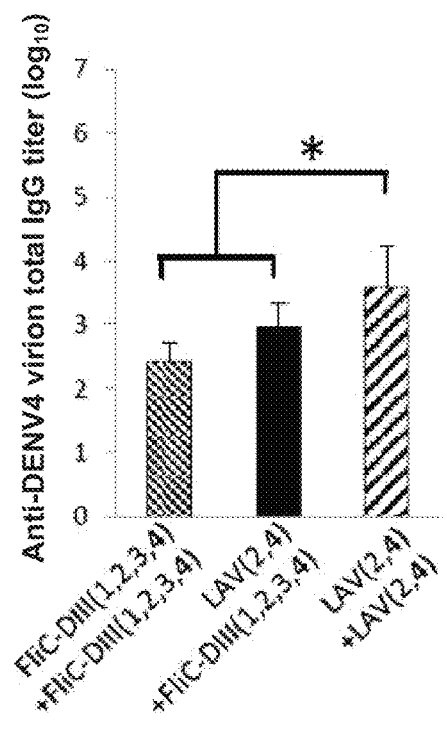
Figure 11A:
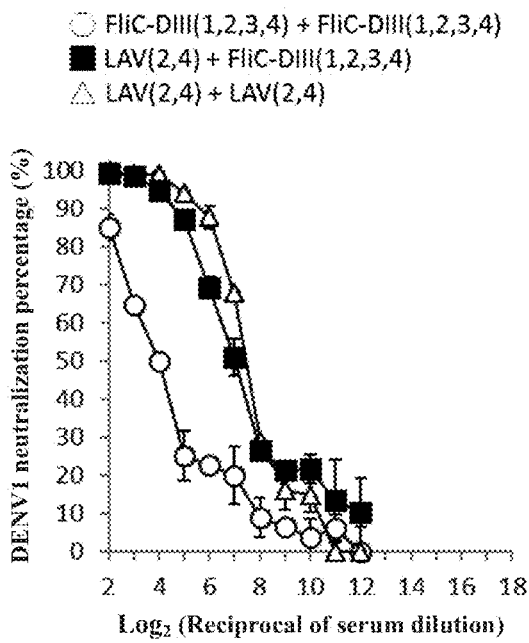
FIGS. 11A-11D show neutralization curves determined by FRNT for serum neutralizing antibodies against dengue virus type 1, type 2, type 3, or type 4 in AG129 mice received different immunizations.
Figure 11B:
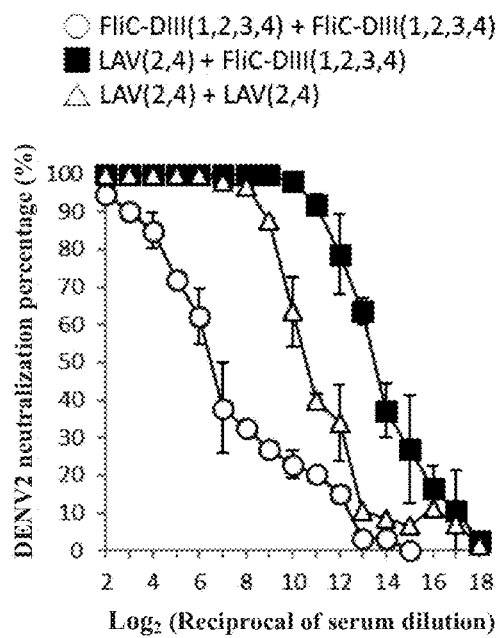
Figure 11C:
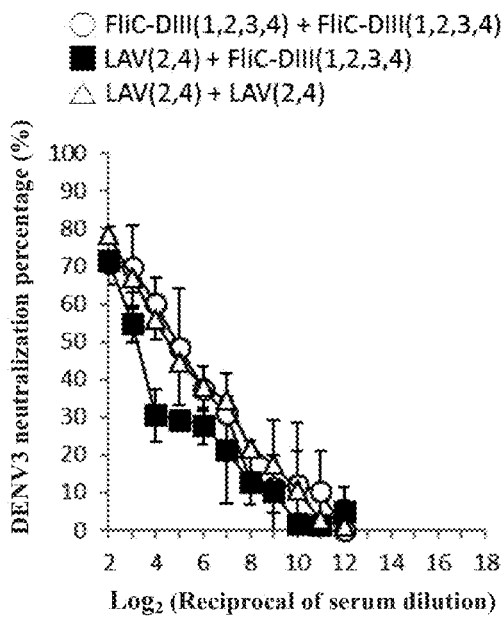
Figure 11D:
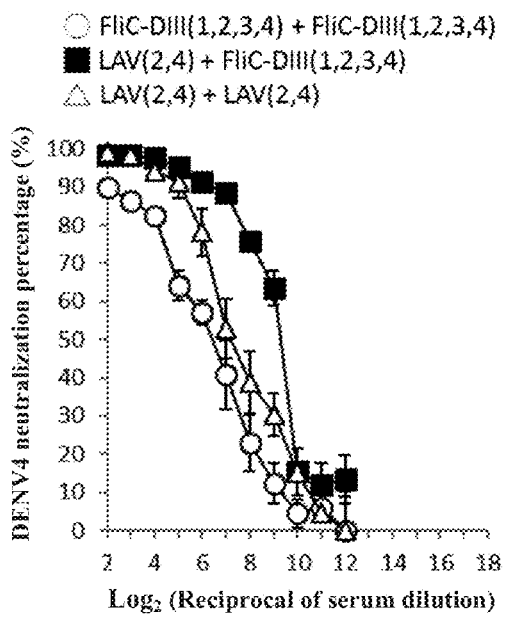
Figure 13A:
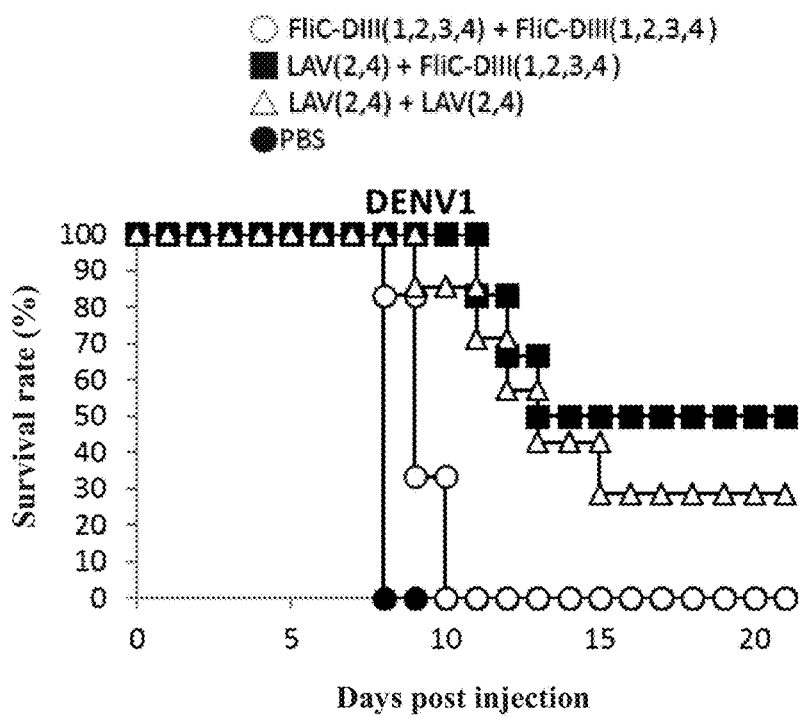
FIGS. 13A-13D show survival curves for 129 suckling mice injected with dengue virus type 1, type 2, type 3, or type 4 that was neutralized by different antisera.
Figure 13B:
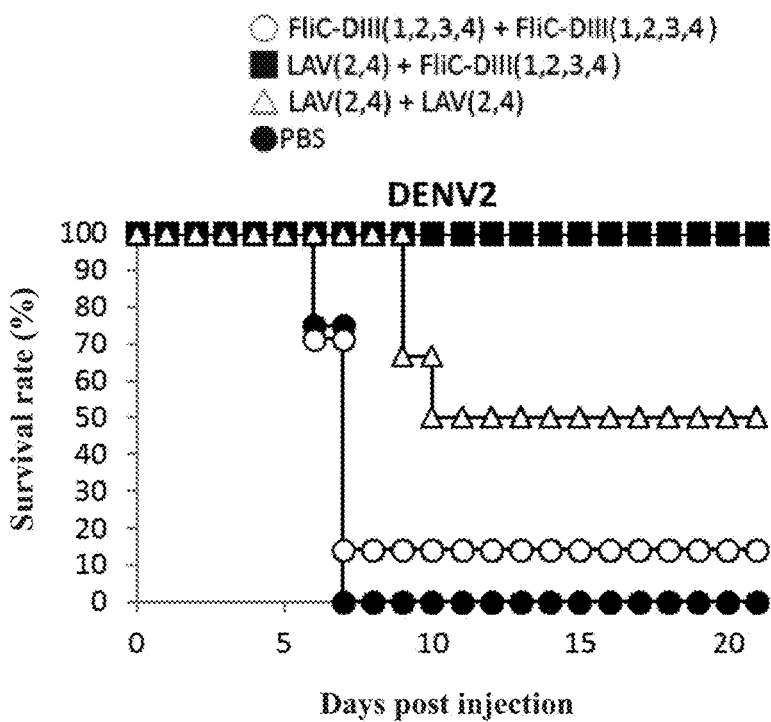
Figure 13C:
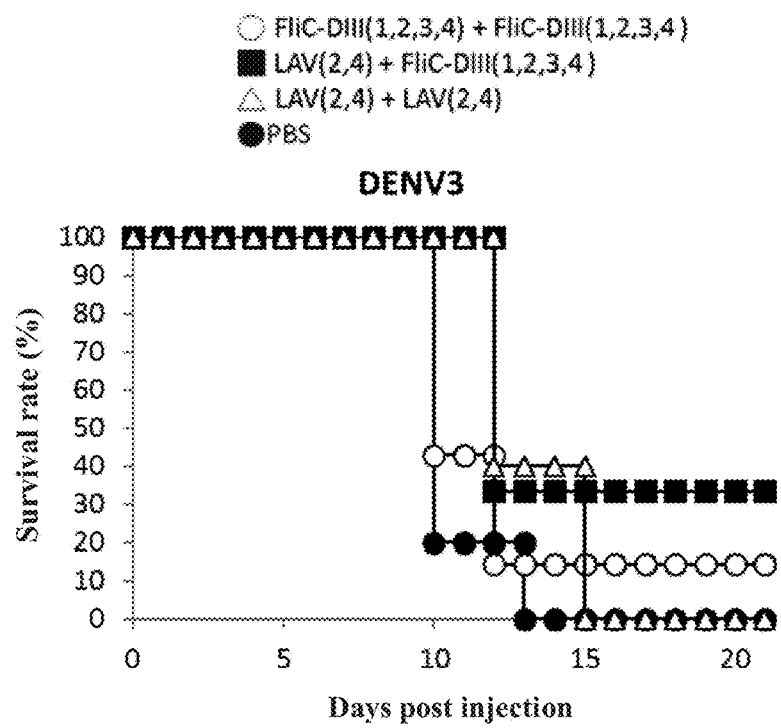
Figure 13D:
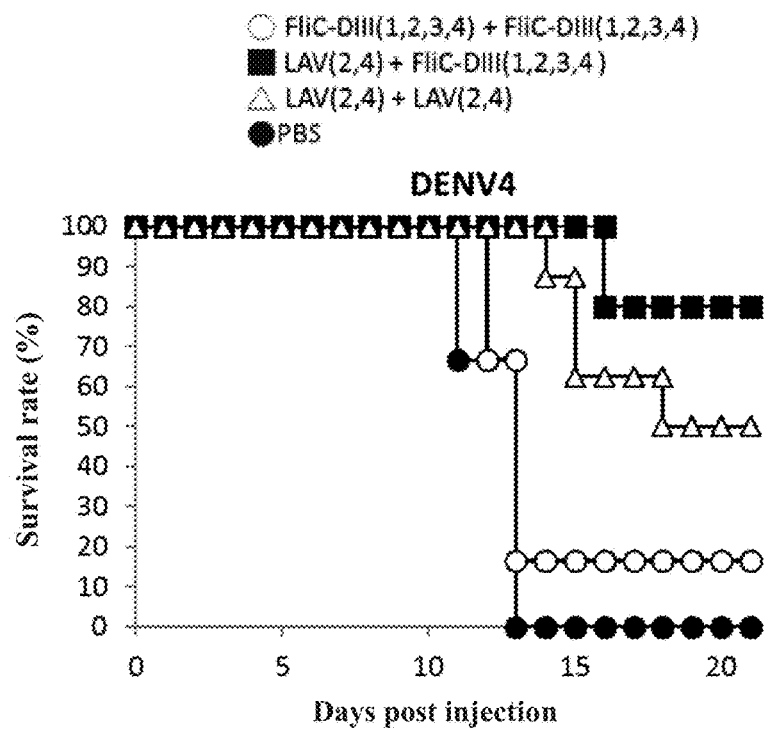
Figure 14A:
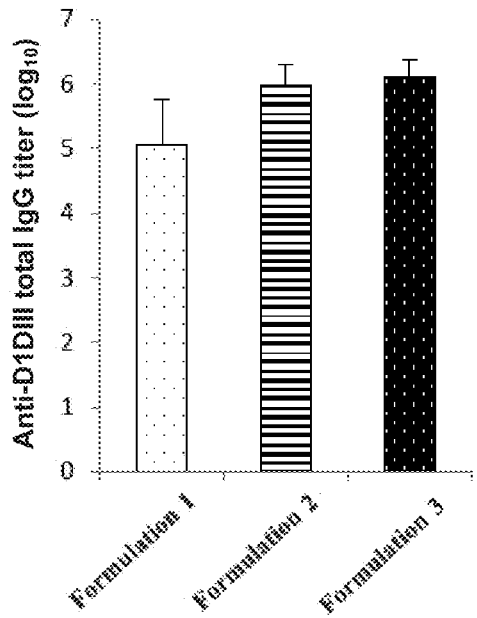
FIGS. 14A-14D show total serum IgG titers determined by ELISA against recombinant envelope domain III protein of dengue virus type 1, type 2, type 3, or type 4 for BALB/c mice receiving different immunizations.
Figure 14B:
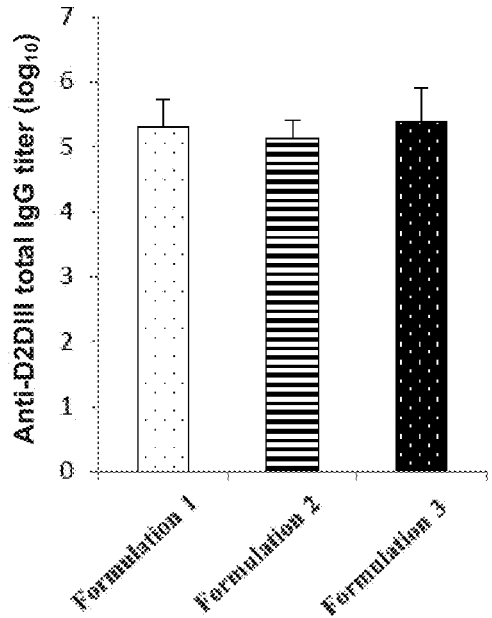
Figure 14C:
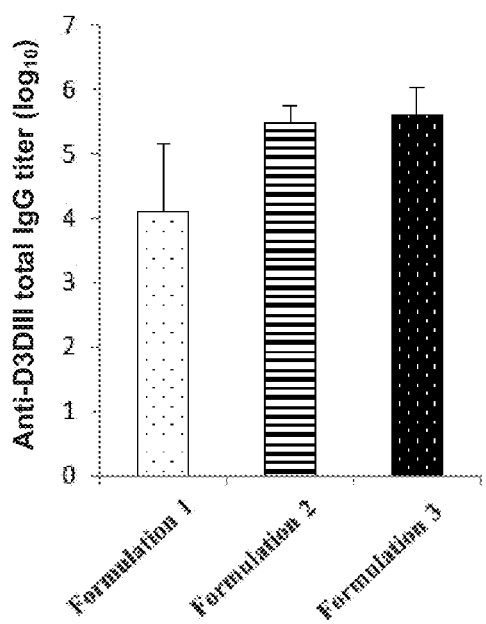
Figure 14D:
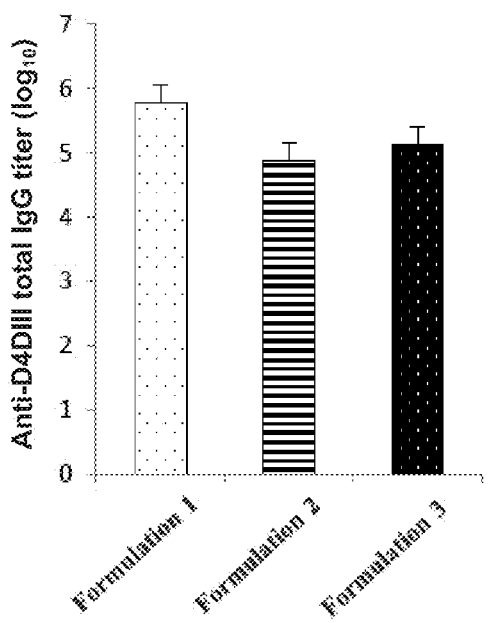
Figure 15A:
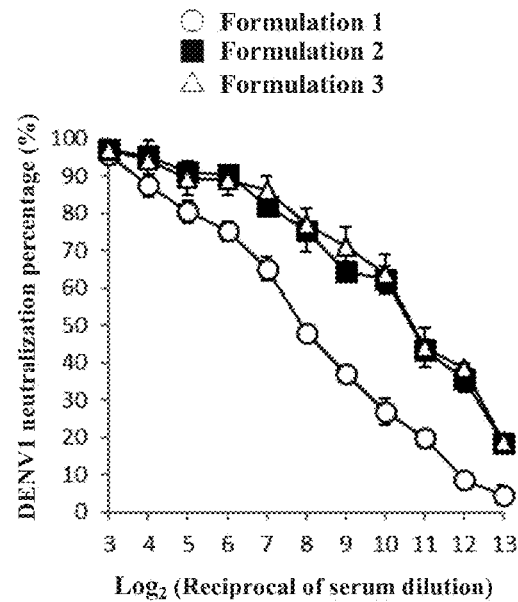
FIGS. 15A-15D show neutralization curves determined by FRNT for serum neutralizing antibodies against dengue virus type 1, type 2, type 3, or type 4 in BALB/c mice received different immunizations.
Figure 15B:
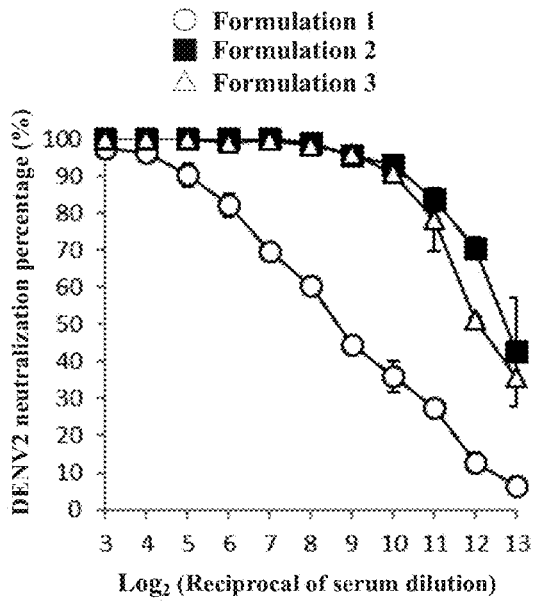
Figure 15C:
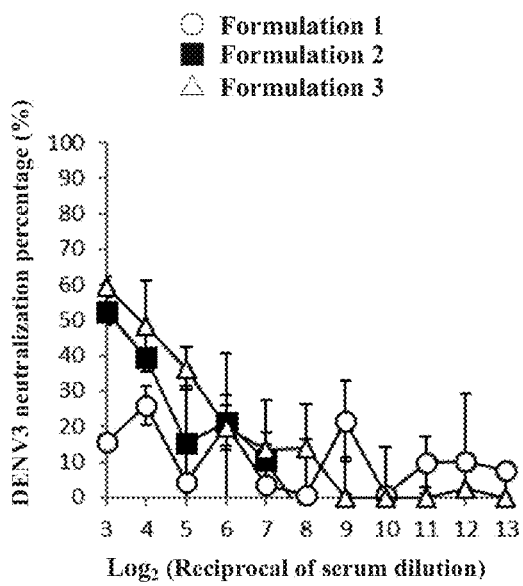
Figure 15D:
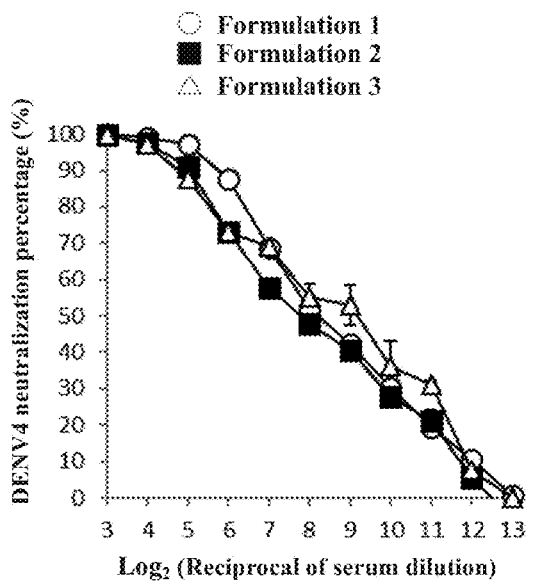
Figure 16A:
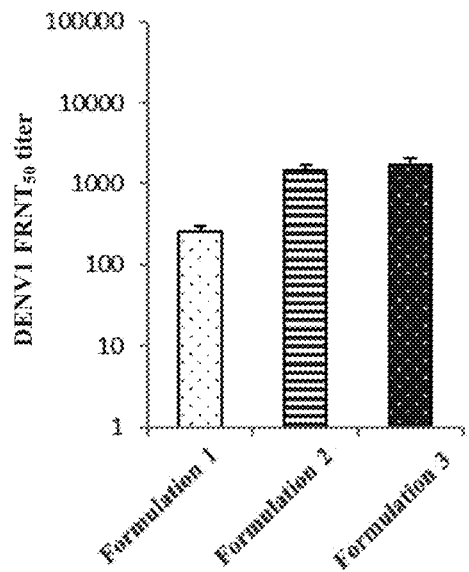
FIGS. 16A-16D show serum neutralizing antibody titers, calculated based on FIGS. 15A-15D, against dengue virus type 1, type 2, type 3, or type 4 for the BALB/c mice receiving different immunizations.
Figure 16B:
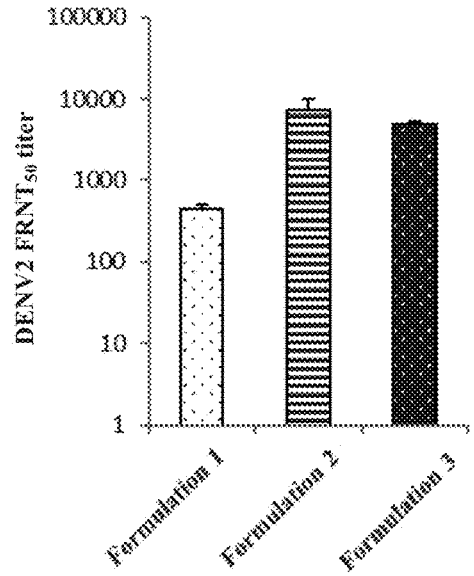
Figure 16C:
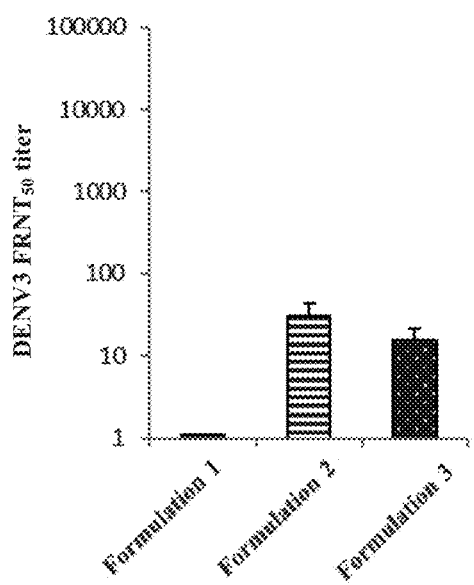
Figure 16D:
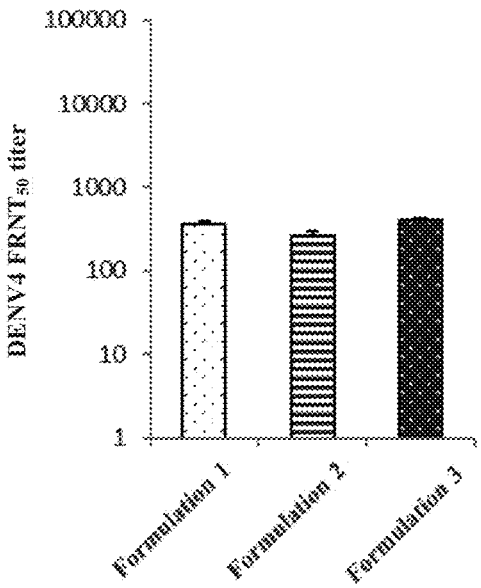

FIGS. 8A-8B shows survival curves for the suckling mice injected with antiserum neutralized DENV2 and DENV4, respectively. According to FIG. 8A, when mice received the heterologous prime-boost immunization with LAV(2,4)+FliC-DIII(2,4) or the homologous prime-boost immunization with LAV(2,4)+LAV(2,4), the antisera therefrom were able to provide protection against DENV2 infection in the suckling mice, leading to a 100% survival rate at 20 days after virus injection to the suckling mice. Comparatively, when mice received the homologous prime-boost immunization with FliC-DIII(2,4)+FliC-DIII(2,4), the antisera therefrom provided poorer protection, resulting in a decreased survival rate of about 30% at 9 days after virus injection to the suckling mice. According to FIG. 8B, when mice were immunized heterologously with LAV(2,4)+FliC-DIII(2,4), the antisera therefrom provided better protection against DENV4 infection in the suckling mice, leading to a survival rate of about 80% at 20 days post virus injection. Comparatively, the antisera from mice immunized homologously with LAV(2,4)+LAV(2,4) provided the suckling mice with poorer protection, resulting in a survival rate of about 60% at 20 days post virus injection; and the antisera from mice immunized homologously with FliC-DIII(2,4)+FliC-DIII(2,4) provided completely no protection against DENV4 infection in the suckling mice. These results once again demonstrated that the heterologous prime-boost immunization of mice with a first vaccine containing the DENV2/4 Δ30 and DENV4 Δ30 viruses followed by a second vaccine containing the recombinant fusion proteins FliC-D2DIII and FliC-D4DIII produced the more effective antisera that protected the suckling mice against infection by multiple dengue virus serotypes.

Example 5

A Vaccine Combination Including a Divalent First Vaccine Containing the Live-Attenuated Dengue Viruses and a Tetravalent Second Vaccine Containing the Recombinant Flagellin and Envelope Domain III Fusion Proteins 5.1 Assessment of Total IgG Titers Against Recombinant Envelope Domain III Proteins According to similar procedures described in Example 4, total serum IgG titers against recombinant DIII proteins were first evaluated in this example after AG129 mice were injected, based on either homologous or heterologous prime-boost immunization strategies, with the live-attenuated dengue virus DENV4 Δ30 and the live-attenuated chimeric dengue virus DENV2/4 Δ30, or the recombinant FliC-DIII fusion proteins of dengue virus type 1, 2, 3, and 4, or the combination of the abovementioned two items. TABLE 2 shows different immunization regimens for mice, including (a) two doses of the recombinant fusion proteins FliC-D1DIII, FliC-D2DIII, FliC-D3DIII, and FliC-D4DIII (denoted as FliC-DIII (1,2,3,4)+FliC-DIII(1,2,3,4)); (b) priming with the DENV2/4 Δ30 and DENV4 Δ30 viruses followed by boosting with the recombinant fusion proteins FliC-D1DIII, FliC-D2DIII, FliC-D3DIII, and FliC-D4DIII (denoted as LAV(2,4)+FliC-DIII(1,2,3,4)), wherein the DENV2/4 Δ30 virus and the DENV4 Δ30 virus were mixed at a number ratio of 2:1 to 1:2, and they were mixed at 1:1 in one embodiment of the present invention; (c) two doses of the DENV2/4 Δ30 and DENV4 Δ30 viruses (denoted as LAV(2,4)+LAV(2,4)). The time interval between the prime and boost immunizations for each immunization regimen was about 1-5 weeks. In one preferred embodiment, the time interval was 3 weeks. Blood samples were collected from the mice two weeks after the boost immunization to obtain the sera.

TABLE 2

| Formulations | Prime | Boost |
|---|---|---|
| FliC-DIII(1,2,3,4) + FliC-DIII(1,2,3,4) | FliC-D1DIII 20 μg/mouse FliC-D2DIII 20 μg/mouse FliC-D3DIII 20 μg/mouse FliC-D4DIII 20 μg/mouse | FliC-D1DIII 20 μg/mouse FliC-D2DIII 20 μg/mouse FliC-D3DIII 20 μg/mouse FliC-D4DIII 20 μg/mouse |
| LAV(2,4) + FliC-DIII(1,2,3,4) | DENV2/4 Δ30 $10^4$ FFU/mouse DENV4 Δ30 $10^4$ FFU/mouse | FliC-D1DIII 20 μg/mouse FliC-D2DIII 20 μg/mouse FliC-D3DIII 20 μg/mouse FliC-D4DIII 20 μg/mouse |
| LAV(2,4) + LAV(2,4) | DENV2/4 Δ30 $10^4$ FFU/mouse DENV4 Δ30 $10^4$ FFU/mouse | DENV2/4 Δ30 $10^4$ FFU/mouse DENV4 Δ30 $10^4$ FFU/mouse |

After the mice were immunized with the three formulations according to TABLE 2, total serum IgG titers against the recombinant DIII protein of dengue virus type 1, type 2, type 3, or type 4 were determined by ELISA, and the results were shown in FIGS. 9A-9D, in which * represents $p<0.05$. According to FIGS. 9A-9D, when compared with the homologous prime-boost immunization with LAV(2,4)+LAV(2,4), the heterologous prime-boost immunization with LAV(2,4)+FliC-DIII(1,2,3,4) or the homologous prime-boost immunization with FliC-DIII (1,2,3,4)+FliC-DIII(1,2,3,4) elicited the higher total serum IgG titers against the four types of recombinant DIII proteins. More specifically, among the IgG elicited by the heterologous prime-boost immunization with LAV(2,4)+FliC-DIII(1,2,3,4), the titer against D1DIII was 40533, the titer against D2DIII was 93866, the titer against D3DIII was 20800, and the titer against D4DIII was 40533. Among the IgG elicited by the homologous prime-boost immunization with FliC-DIII (1,2,3,4)+FliC-DIII(1,2,3,4), the titer against D1DIII was 36450, the titer against D2DIII was 35198, the titer against D3DIII was 30983, and the titer against D4DIII was 35198.

In this example, total serum IgG titers against the virion of dengue virus type 1, type 2, type 3, or type 4 were also determined by ELISA and the results were shown in FIGS. 10A-10D, in which * represents $p<0.05$. For experiments, the ELISA plates were coated with $10^4$ FFU of the formalininactivated dengue virus (100 μl/well). According to FIGS. 10A-10D, when compared with the heterologous prime-boost immunization with LAV(2,4)+FliC-DIII(1,2,3,4) or the homologous prime-boost immunization with FliC-DIII (1,2,3,4)+FliC-DIII(1,2,3,4), the homologous prime-boost immunization with LAV(2,4)+LAV(2,4) elicited the higher total serum IgG titers against the four types of dengue virus virions, including a titer of 7800 against DENV1 virion, a titer of 7800 against DENV2 virion, a titer of 7800 against DENV3 virion, and a titer of 3900 against DENV4 virion.

5.2 Assessment of Neutralizing Antibody Titers Against Dengue Virus

Focus reduction neutralizing test was performed in this example to further compare the neutralization curves and titers for the serum neutralizing antibodies against dengue virus type 1, type 2, type 3, or type 4 after AG129 mice were immunized with the three formulations according to TABLE 2. The neutralization curves were shown in FIGS. 11A-11D. The neutralizing antibody titers were shown in FIGS. 12A-12D, in which * represents p<0.05. According to FIGS. 11A-11D, the heterologous prime-boost immunization of mice with a first vaccine containing the DENV2/4 Δ30 and DENV4 Δ30 viruses followed by a second vaccine containing the recombinant fusion proteins FliC-D1DIII, FliC-D2DIII, FliC-D3DIII, and FliC-D4DIII elicited the higher titers of serum neutralizing antibodies against multiple dengue virus serotypes, particularly against dengue virus type 2 and type 4. FIGS. 12A-12D further shows that the above-mentioned heterologous prime-boost immunization elicited the highest titers of mouse serum neutralizing antibodies against dengue virus type 2 and type 4, including a titer of 12899 against DENV2 and a titer of 553 against DENV4.

5.3 Protection of Antisera Against Dengue Virus

Sucking mice assay was performed in this example to further examine the protection against dengue virus type 1, type 2, type 3, or type 4 in sucking mice that was provided by the antisera from AG129 mice immunized with the three formulations according to TABLE 2. FIGS. 13A-13D shows survival curves for the suckling mice injected with antiserum neutralized DENV1, DENV2, DENV3, and DENV4, respectively.

According to FIGS. 13A-13D, when mice received the heterologous prime-boost immunization with LAV(2,4)+FliC-DIII(1,2,3,4), the antisera therefrom were able to provide better protection against DENV1, DENV2, DENV3, and DENV4 infection in the suckling mice, leading to the survival rates of about 50%, 100%, about 35%, and about 80%, respectively at 20 days after virus injection. Comparatively, the antisera from mice immunized homologously with LAV(2,4)+LAV(2,4) or FliC-DIII(1,2,3,4)+FliC-DIII(1,2,3,4) provided the suckling mice with poorer protection against DENV1, DENV2, DENV3, and DENV4 infection. These results showed that the heterologous prime-boost immunization with LAV(2,4)+FliC-DIII(1,2,3,4) provided the best protection against dengue virus type 2 and type 4, similar to the results of the assessment of neutralizing antibody titers against dengue virus. The results also demonstrated that the heterologous prime-boost immunization of mice with a first vaccine containing the DENV2/4 Δ30 and DENV4 Δ30 viruses followed by a second vaccine containing the recombinant fusion proteins FliC-D1DIII, FliC-D2DIII, FliC-D3DIII, and FliC-D4DIII produced the more effective antisera that protected the suckling mice against infection by multiple dengue virus serotypes.

Example 6

A Vaccine Combination Including a Tetravalent First Vaccine Containing the Adenoviral Vectors Expressing Precursor Membrane Protein and Envelope Protein and a Tetravalent Second Vaccine Containing the Recombinant Flagellin and Envelope Domain III Fusion Proteins or a Divalent Second Vaccine Containing the Live-Attenuated Dengue Viruses 6.1 Assessment of Total IgG Titers Against Recombinant Envelope Domain III Proteins According to similar procedures described in example 4, total serum IgG titers against recombinant DIII proteins were first evaluated in this example after BALB/c mice were injected, based on heterologous prime-boost immunization strategy, with various combinations of the following at different doses: the adenoviral vectors expressing prM and E proteins of dengue virus type 1, 2, 3, and 4 (referred to as Ad-D1 prME, Ad-D2 prME, Ad-D3 prME, and Ad-D4 prME, respectively), the recombinant FliC-DIII fusion proteins of dengue virus type 1, 2, 3, and 4, and the live-attenuated dengue virus DENV4 Δ30 and the live-attenuated chimeric dengue virus DENV2/4 Δ30. TABLE 3 shows different immunization regimens for mice, including (a) priming with equivalent amounts of the adenoviral vectors Ad-D1 prME, Ad-D2 prME, Ad-D3 prME, and Ad-D4 prME followed by boosting with the recombinant fusion proteins FliC-D1DIII, FliC-D2DIII, FliC-D3DIII, and FliC-D4DIII (denoted as Formulation 1); (b) priming with the adenoviral vectors Ad-D1 prME, Ad-D2 prME, Ad-D3 prME, and Ad-D4 prME followed by boosting with the recombinant fusion proteins FliC-D1DIII, FliC-D2DIII, FliC-D3DIII, and FliC-D4DIII, wherein the amount of Ad-D3 prME was five times the amount of each of the other adenoviral vectors (denoted as Formulation 2); (c) priming with the adenoviral vectors Ad-D1 prME, Ad-D2 prME, Ad-D3 prME, and Ad-D4 prME followed by boosting with the DENV2/4 Δ30 and DENV4 Δ30 viruses, wherein the amounts of Ad-D1 and prME Ad-D3 prME were five times and ten times, respectively, the amount of each of the other two adenoviral vectors (denoted as Formulation 3). The time interval between the prime and boost immunizations for each immunization regimen was about 1-5 weeks. In one preferred embodiment, the time interval was 3 weeks. Blood samples were collected from the mice two weeks after the boost immunization to obtain the sera.

TABLE 3

| Formulations | Prime | Boost |
|---|---|---|
| 1 | Ad-D1 prME $10^8$ PFU/mouse | FliC-D1 DIII 20 μg/mouse |
|   | Ad-D2 prME $10^8$ PFU/mouse | FliC-D2 DIII 20 μg/mouse |
|   | Ad-D3 prME $10^8$ PFU/mouse | FliC-D3 DIII 20 μg/mouse |
|   | Ad-D4 prME $10^8$ PFU/mouse | FliC-D4 DIII 20 μg/mouse |
| 2 | Ad-D1 prME $10^8$ PFU/mouse | FliC-D1 DIII 20 μg/mouse |
|   | Ad-D2 prME $10^8$ PFU/mouse | FliC-D2 DIII 20 μg/mouse |
|   | Ad-D3 prME $5 \times 10^8$ PFU/mouse | FliC-D3 DIII 20 μg/mouse |
|   | Ad-D4 prME $10^8$ PFU/mouse | FliC-D4 DIII 20 μg/mouse |

TABLE 3-continued

| Formulations | Prime | Boost |
|---|---|---|
| 3 | Ad-D1 prME 5 × 10$^8$ PFU/mouse<br>Ad-D2 prME 10$^8$ PFU/mouse<br>Ad-D3 prME 10$^9$ PFU/mouse<br>Ad-D4 prME 10$^8$ PFU/mouse | DENV2/4 Δ30 10$^4$ FFU/mouse<br>DENV4 Δ30 10$^4$ FFU/mouse |

After the mice were immunized with the three formulations according to TABLE 3, total serum IgG titers against the recombinant DIII protein of dengue virus type 1, type 2, type 3, or type 4 were determined by ELISA, and the results were shown in FIGS. 14A-14D. According to FIGS. 14A-14D, the heterologous prime-boost immunization of mice with either one of the three formulations previously described elicited high total serum IgG titers against the four types of recombinant DIII proteins. More specifically, among the IgG elicited by Formulation 1, the titer against D1DIII was 117626, the titer against D2DIII was 204800, the titer against D3DIII was 12800, and the titer against D4DIII was 620837. Among the IgG elicited by Formulation 2, the titer against D1DIII was 941013, the titer against D2DIII was 135117, the titer against D3DIII was 310418, and the titer against D4DIII was 77604. Among the IgG elicited by Formulation 3, the titer against D1DIII was 1241675, the titer against D2DIII was 235253, the titer against D3DIII was 409600, and the titer against D4DIII was 135117.

6.2 Assessment of Neutralizing Antibody Titers Against Dengue Virus

Focus reduction neutralizing test was performed in this example to further compare the neutralization curves and titers for the serum neutralizing antibodies against dengue virus type 1, type 2, type 3, or type 4 after BALB/c mice were immunized with the three formulations according to TABLE 3. The neutralization curves were shown in FIGS. 15A-15D. The neutralizing antibody titers were shown in FIGS. 16A-16D. According to FIGS. 15A-15D, the heterologous prime-boost immunization of mice with a first vaccine and a second vaccine according to Formulation 2 or Formulation 3 elicited the higher titers of serum neutralizing antibodies against dengue virus type 1 and type 2. FIGS. 16A-16D further shows that Formulation 2 and Formulation 3 elicited high titers of mouse serum neutralizing antibodies against dengue virus type 1, type 2, and type 4, particularly against dengue virus type 2. Among the neutralizing antibodies elicited by Formulation 2, the titer against DENV1 was 1460, the titer against DENV2 was 7361, and the titer against DENV4 was 264. Among the IgG elicited by Formulation 3, the titer against DENV1 was 1693, the titer against DENV2 was 4878, and the titer against DENV4 was 412.

In conclusion, the vaccine combination of the present invention includes a first vaccine containing a live-attenuated dengue virus and a live-attenuated chimeric dengue virus and a second vaccine containing a plurality type of recombinant flagellin and envelope domain III fusion proteins. This combination, such as the divalent first vaccine and the divalent second vaccine in Example 4, and the divalent first vaccine and the tetravalent second vaccine in Example 5, can effectively elicit neutralizing antibodies against the four dengue virus serotypes in a subject based on heterologous prime-boost immunization. Therefore, it may enhance immunity against viral infection by the four dengue virus serotypes in a subject. The vaccine combination of the present invention may also include a first vaccine containing a plurality type of adenoviral vectors expressing a precursor membrane protein and an envelope protein and a second vaccine containing a plurality type of recombinant flagellin and envelope domain III fusion proteins or a combination of a live-attenuated dengue virus and a live-attenuated chimeric dengue virus to effectively elicit neutralizing antibodies against multiple dengue virus serotypes in a subject based on heterologous prime-boost immunization. Moreover, the present invention has demonstrated that among the neutralizing antibodies elicited by the vaccine combination, the antibodies specific for envelope domain III are the major contributors to the ability of the neutralizing antibodies to neutralize dengue virus.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method of preventing or treating viral infection by multiple dengue virus serotypes in a subject comprising the steps of (a) administering to the subject a first vaccine comprising viruses consisting of a live-attenuated dengue virus type 4 and a live-attenuated type 2/type 4 chimeric dengue virus; and (b) administering to the subject a second vaccine comprising a plurality type of recombinant flagellin and envelope domain III fusion proteins consisting of a recombinant flagellin-dengue virus type 1 envelope domain III fusion protein, a recombinant flagellin-dengue virus type 2 envelope domain III fusion protein, a recombinant flagellin-dengue virus type 3 envelope domain III fusion protein, and a recombinant flagellin-dengue virus type 4 envelope domain III fusion protein, wherein each type of the recombinant flagellin and envelope domain III fusion proteins comprises one copy of an envelope domain III; wherein the vaccine combination provides protection against more dengue virus serotypes than the live-attenuated dengue viruses in the first vaccine.

2. The method of claim 1, wherein the live-attenuated dengue virus type 4 is in an amount of at least 10$^4$ FFU.

3. The method of claim 1, wherein the live-attenuated type 2/type 4 chimeric dengue virus is in an amount of at least 10$^4$ FFU.

4. The method of claim 1, wherein live-attenuated type 2/type 4 chimeric dengue virus expresses a precursor membrane protein and an envelope protein both derived from dengue virus type 2.

5. The method of claim 1, wherein each of the recombinant flagellin and envelope domain III fusion proteins is in an amount of at least 20 μg.

6. The method of claim 1, wherein the second vaccine is administered 1-5 weeks after the first vaccine.

* * * * *